US008129357B2

(12) United States Patent
Chern et al.

(10) Patent No.: US 8,129,357 B2
(45) Date of Patent: Mar. 6, 2012

(54) METHOD OF MAKING AND USING AN ADENOSINE ANALOGUE

(75) Inventors: Yijuang Chern, Taipei (TW); Yun-Lian Lin, Taipei (TW); Nai-Kuei Huang, Taipei (TW); Jung-Hsing Lin, Taipei (TW); Jim-Min Fang, Taipei (TW); Chia-I Lin, Taipei (TW)

(73) Assignee: Academia Sinica, Taipei (TW)

( * ) Notice: Subject to any disclaimer, the term of this patent is extended or adjusted under 35 U.S.C. 154(b) by 551 days.

(21) Appl. No.: 11/999,637

(22) Filed: Dec. 6, 2007

(65) Prior Publication Data

US 2008/0176816 A1 Jul. 24, 2008

Related U.S. Application Data

(63) Continuation-in-part of application No. 11/400,064, filed on Apr. 7, 2006, now Pat. No. 7,351,434.

(51) Int. Cl.
*A61K 36/00* (2006.01)
*A61K 36/8988* (2006.01)
*A61K 31/70* (2006.01)

(52) U.S. Cl. .......................................... 514/46; 424/725
(58) Field of Classification Search ........................ None
See application file for complete search history.

(56) References Cited

U.S. PATENT DOCUMENTS 6,875,769 B2 * 4/2005 Chen .............................. 514/256

FOREIGN PATENT DOCUMENTS

KR 2004064240 A * 7/2004
WO WO 2004/058791 A2 * 7/2004

OTHER PUBLICATIONS

Giulian et al, Specific domains of beta-amyloid from Alzheimer plaque elicit neuron killing in human microglia, The Journal of neuroscience: the official journal of the Society for Neuroscience 16 (19): 6021-37, 1996.*
Ryu et al, Peripheral benzodiazepine receptor ligand PK11195 reduces microglial activation and neuronal death in quinolinic acid-injected rat striatum, Neurobiology of disease, (Nov. 2005) vol. 20, No. 2, pp. 550-561.*
Hardy et al, genetic classification of primary neurodegenerative disease, Science, 282 (6): 1075-1079.*
Vippagunta et al, Crystalline Solids, Advanced Drug Delivery Reviews, 2001, 48, 1-26.*
Braga et al, Making Crystals from Crystals: a green route to crystal engineering and polymorphism, Chem Commun 2005, pp. 3635-3645.*
Seddon, K.R., Pseudopolymorph: a polemic, Crystal Growth & Design, 2004, 4(6), pp. 1087, web release date Oct. 19, 2004.*
Hardy et al, genetic classification of primary neurodegenerative disease, Science, 282 (6): 1075-1079. 1998.*
An, et al., Gastrodin Decreases Immunoreactivities of γ-Aminobutyric Acid Shunt Enzymes in the Hippocampus of Seizures-Sensitive Gerbils, (2003) *J Neurosci Res.* 71, 534-43.
Barbeito, L.H., et al. A role for astrocytes in motor neuron loss in amyotrophic lateral sclerosis. *Brain Res Brain Res Rev* 47, 263-274 (2004).
Chandra, A., Enkhbaatar, P., Nakano, Y., Traber, L.D. & Traber, D.L. Sepsis: emerging role of nitric oxide and selectins. *Clinics* 61, 71-76 (2006).
Chou, et al., CGS21680 attenuates symptoms of Huntington's disease in a transgenic mouse model, (2005) *J Neurochem* 93, 310-20.
Deckel, A.W. Nitric oxide and nitric oxide synthase in Huntington's disease. *J Neurosci Res* 64, 99-107 (2001).
Hayashi, et al., Phenolic compounds from *Gastrodia rhizome* and relaxant effects of related compounds on isolated smooth muscle preparation, (2002) *Phytochemistry* 59, 513-9.
Huang, et al., *Gastrodia elata* prevents rat pheochromocytoma cells from serum-deprived apoptosis: the role of the MAPK family (2004) *Life Sci* 75, 1649-57.
Huang, N.K., et al. Neuroprotective principles from *Gastrodia elata*. *J Nat Prod* 70, 571-574 (2007).
Hsieh et al, Anticonvulsive and free radical scavenging activities of vanillyl alcohol in ferric chloride-induced epileptic seizures in Sprague-Dawley rats, *Life Sciences* 67 (2000) 1185-1195.
Kim, et al., Ether Fraction of Methanol Extracts of *Gastrodia elata*, Medicinal Herb Protects against Neuronal Cell Damage after Transient Global Ischemia in Gerbils (2003) *Phytother Res* 17, 909-12.
Marchetti, B., et al. Glucocorticoid receptor-nitric oxide crosstalk and vulnerability to experimental parkinsonism: pivotal role for glia-neuron interactions. *Brain Res Brain Res Rev* 48, 302-321 (2005).
Sastre, et al., Contribution of inflammatory processes to Alzheimer's disease: molecular mechanisms, *Int. J. Devil Neuroscience* 24 (2006) 167-176.
Deckel, A. Wallace, Nitric Oxide and Nitric Oxide Synthase in Huntington's Disease, *Journal of Neuroscience Research* 64:99-107 (2001).
Kim et al., Ether Fraction of methanol Extracts of *Gastrodia elata*, medicinal Herb Protects against Neuronal Cell Damage after Transient Global Ischemia in Gerbils, *Phytother. Res.* 17, 909-912 (2003).
Marchetti et al., Glucocorticoid receptor-nitric oxide crosstalk and vulnerability to experimental parkinsonism: pivotal role for glia-neuron interactions, *Brain Research Reviews* 48 (2005) 302-321.
Sastre, et al., Contribution of inflammatory process to Alzheimer's disease: molecular mechanisms, *Int. J. Devl. Neuroscience* 24 (2006) 167-176.
An et al., Gastrodin Decreases Immunoreactivities of γ-Aminobutyric Acid Shunt Enzymes in the Hippocampus of Seizure-Sensitive Gerbils, *Journal of Neuroscience Research* 71:534-543 (2003).
Barbeito et al., A role for astrocytes in motor neuron loss in amyotrophic lateral sclerosis, *Brain Research Reviews* 47 (2004) 263-274.

(Continued)

*Primary Examiner* — Qiuwen Mi

(57) ABSTRACT

This document describes compounds, extracts, and pharmaceutical compositions relating to *Gastrodia* spp., and methods for the treatment subjects having metabolic disorders or medical conditions such as Huntington's disease, a trinucleotide repeat disease or abnormal blood glucose levels.

4 Claims, 24 Drawing Sheets

OTHER PUBLICATIONS

Chandra et al., Sepsis: Emerging Role of Nitric Oxide and Selectins, *Clinics* 2006:61(1):71-6.

Hayashi et al., Phenolic compounds from *Gastrodia rhizome* and relaxant effects of related compounds on isolated smooth muscle preparation, *Phytochemistry* 59 (2002) 513-519.

Hsieh et al., Anticonvulsive and free radical scavenging activities of vanillyl alcohol in ferric chloride-induced epileptic seizures in Sprague-Dawley rats, *Life Sciences* 67 (2000) 1185-1195.

Huang et al., Neuroprotective Principles from *Gastrodia elata*, *J. Nat. Prod.* 2007, 70:571-574.

Huang et al., *Gastrodia elata* prevents rat pheochromocytoma cells from serum-deprived apoptosis: the role of the MAPK family, *Life Sciences* 75 (2004) 1649-1657.

Chou et al., CGS21680 attenuates symptoms of Huntington's disease in a transgenic mouse model, *Journal of Neurochemistry* 2005, 93: 310-320 (2005).

* cited by examiner

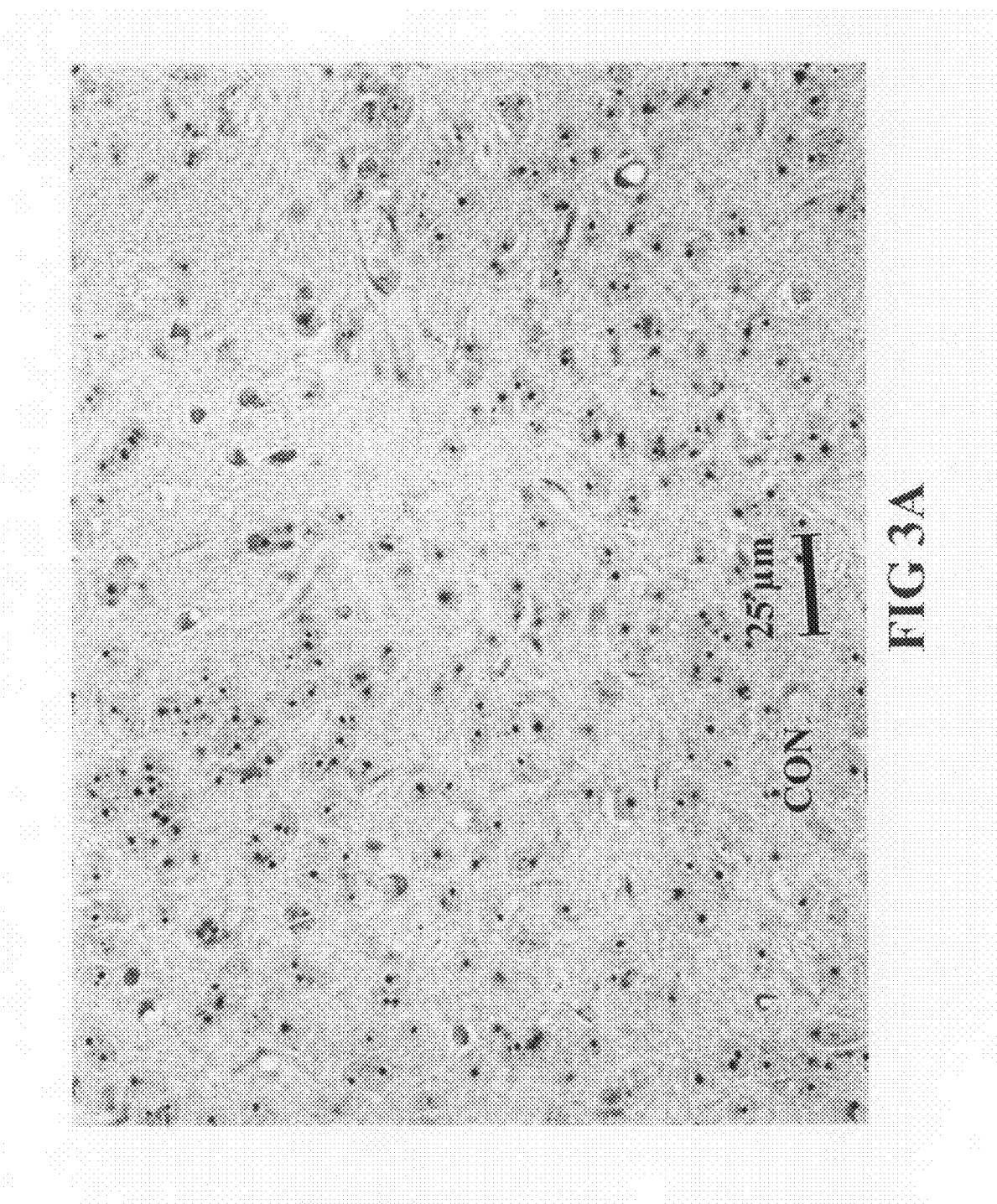

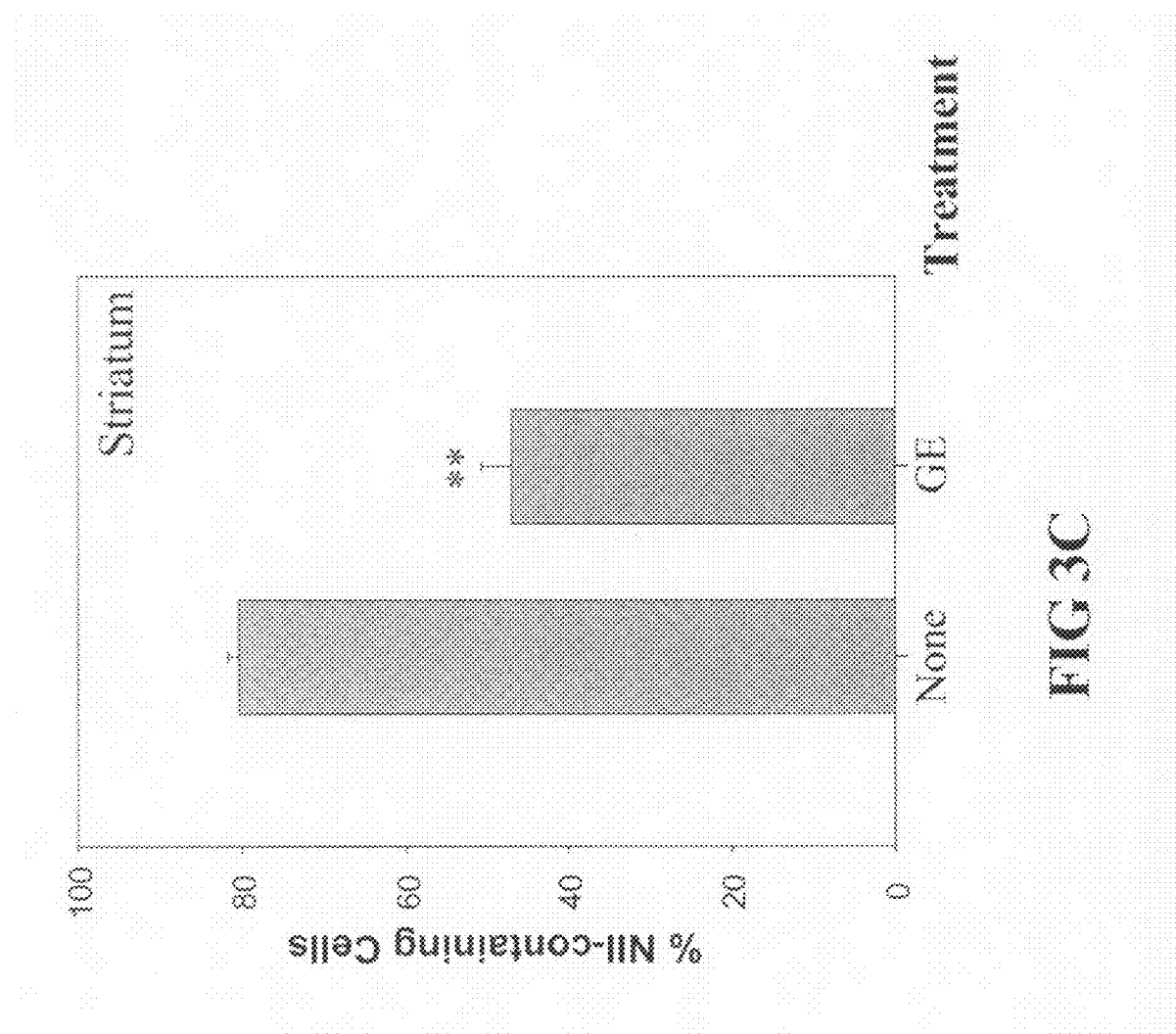

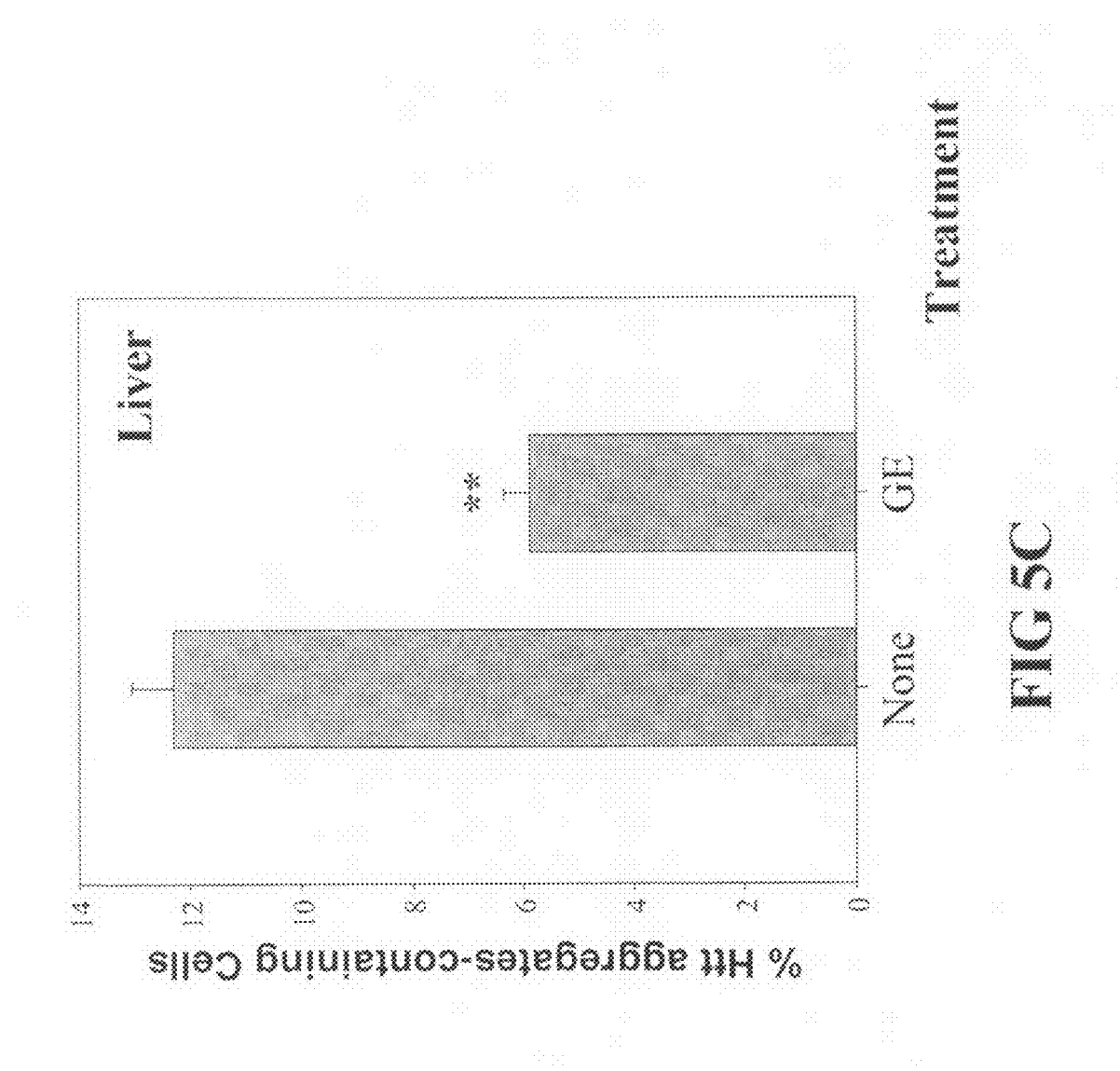

Fig. 12. $^{13}$C NMR spectrum of compound 1 (CD$_3$OD, 400 MHz)

Fig. 13. ¹H NMR spectrum of compound 2 (DMSO-$d_6$, 400 MHz)

Fig. 14. $^{13}$C NMR spectrum of compound 2 (DMSO-$d_6$, 400 MHz)

Fig. 15. $^1$H NMR spectrum of compound 5 (DMSO-$d_6$, 400 MHz)

SEQUENCE LISTING

```
<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ccgctcaggt tctgctttta                                              20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggctgaggaa gctgaggag                                               19
```

METHOD OF MAKING AND USING AN ADENOSINE ANALOGUE

CROSS REFERENCE TO RELATED APPLICATIONS

This application is a continuation-in-part of U.S. patent application Ser. No. 11/400,064 which was filed with the U.S. Patent and Trademark Office on Apr. 7, 2006 now U.S. Pat. No. 7,351,434. The content of U.S. patent application Ser. No. 11/400,064 is herein incorporated as reference in its entirety.

BACKGROUND OF THE INVENTION

1. Field of the Invention

This document describes compounds, extracts, and pharmaceutical compositions relating to *Gastrodia* spp., and methods for the treatment of subjects having metabolic disorders or diseases such as Huntington's disease.

References

An, et al. (2003) J Neurosci Res 71, 534-43
Baker, et al., "Controlled Release of Biological Active Agents", John Wiley and Sons, 1986.
Barbeito, L. H., et al. A role for astrocytes in motor neuron loss in amyotrophic lateral sclerosis. *Brain Res Brain Res Rev* 47, 263-274 (2004).
Bates, G. (2003) Lancet 361, 1642-4.
Beattie, M. S. Inflammation and apoptosis: linked therapeutic targets in spinal cord injury. *Trends Mol Med* 10, 580-583 (2004).
Blanco, A. M. & Guerri, C. Ethanol intake enhances inflammatory mediators in brain: role of glial cells and TLR4/IL-1RI receptors. *Front Biosci* 12, 2616-2630 (2007).
Borovecki, F. et al. (2005) Proc Natl Acad Sci USA 102, 11023-8.
Calabrese, V., Boyd-Kimball, D., Scapagnini, G. & Butterfield, D. A. Nitric oxide and cellular stress response in brain aging and neurodegenerative disorders: the role of vitagenes. *In Vivo* 18, 245-267 (2004).
Carter, et al. (1999) J Neurosci 19, 3248-57.
Chandra, A., Enkhbaatar, P., Nakano, Y., Traber, L. D. & Traber, D. L. Sepsis: emerging role of nitric oxide and selecting. *Clinics* 61, 71-76 (2006).
Chou, et al. (2005) J Neurochem 93, 310-20.
Deckel, A. W. Nitric oxide and nitric oxide synthase in Huntington's disease. *J Neurosci Res* 64, 99-107 (2001).
Duan, et al. (2003) Proc Natl Acad Sci USA 100, 2911-6.
Ehrlich, et al. (2001) Exp Neurol 167, 215-26.
Golisade, A. W., J.; Herforth, C.; Jomaab, H.; Linka, A. Bioorg. Anti-malarial activity of $N^6$-substituted adenosine derivatives. Part I. *Med. Chem.* 10, 769-777 (2002).
Greene and Wuts, "Protective Groups in Organic Synthesis", John Wiley & Sons (1991).
Hayashi, et al. (2002) Phytochemistry 59, 513-9.
Holm, et al. (1999) Curr Opin Clin Nutr Metab Care 2, 47-53.
Hsieh, et al. (2000) *Life Sci* 67, 1185-95.
Hsieh, et al. (2001) *Am J Chin Med* 29, 331-41.
Huang, et al. (2004) *Life Sci* 75, 1649-57.
Huang, et al. (2005) Chin. J. Med. Chem. 15, 227-229.
Huang, N. K., et al. Neuroprotective principles from *Gastrodia elata*. *J Nat Prod* 70, 571-574 (2007).
Hurlbert, M. S., Zhou, W., Wasmeier, C., Kaddis, F. G., Hutton, J. C. & Freed, C. R. (1999) *Diabetes* 48, 649-5.
Ishiguro, et al. (2001) J Neurosci Res 65, 289-97.
Kim, et al. (2001) Neurosci Lett 314, 65-8.
Kim, et al. (2003) J Ethnopharmacol 84, 95-8.
Kim, et al. (2003) Phytother Res 17, 909-12.
Larock, R. C. "Comprehensive Organic Transformations: A Guide to Functional Group Preparations", 2nd Ed., Wiley-VCH, New York, 1999.
Lin, et al. (1996) Phytochemistry 42, 549-551.
Mangiarini, et al. (1996) Cell 87, 493-506.
Marchetti, B., et al. Glucocorticoid receptor-nitric oxide crosstalk and vulnerability to experimental parkinsonism: pivotal role for glia-neuron interactions. *Brain Res Brain Res Rev* 48, 302-321 (2005).
Mazzolla, R., et al. Enhanced resistance to *Cryptococcus neoformans* infection induced by chloroquine in a murine model of meningoencephalitis. *Antimicrob Agents Chemother* 41, 802-807 (1997).
Meade, et al. (2002) J Comp Neurol 449, 241-69.
Panov, et al. (2005) Mol Cell Biochem 269, 143-52.
Podolsky, et al. (1972) Lancet 1, 1356-8.
Remington's Pharmaceutical Sciences, Mack Publishing Company, Easton, Pa., 21$^{st}$ edition, 2005.
Taguchi, et al. (1981) Chem. Pharm. Bull. 29, 55-62.
Tanaka, et al. (2004) Nat Med 10, 148-54.
The Huntington's Disease Collaborative Research Group, 1993 Cell 72, 971-83.
Wu, et al. (2004) J Clin Invest 113, 434-40.
Wu, Y., Liu, N. & Long, Q. (1998) Zhong Yao Cai 21, 1-3.
Xiao, et al. (2002) Zhongguo Zhong Yao Za Zhi 27, 35-6.

2. Description of the Related Art

Huntington's disease (HD) is an autosomal dominant neurodegenerative disease characterized by chorea, dementia, and psychiatric symptoms. As the disease progresses, concentration and short-term memory diminish and involuntary movements of the head, trunk, and limbs increase. Walking, speaking, and swallowing abilities deteriorate. Eventual death results from complications such as choking, infection, or heart failure.

The causative mutation is a CAG trinucleotide expansion in exon 1 of the Huntingtin (Htt) gene (Huntington's Disease Collaborative Research Group (1993)). Normal chromosomes have 35 or fewer CAG repeats in the N-terminal region, whereas HD is associated with 36 or more repeats. The expanded CAG repeats are translated into polyglutamine residues (polyQ) in the Htt protein. When the number of CAG repeats exceeds 36, specific degeneration of several brain areas (especially in the striatum) occurs. Formation of Htt aggregates and alteration of overall gene expression profiles have also been reported in peripheral tissues including blood cells, the liver, and kidney (Borovecki, F. et al. (2005); Panov, et al. (2005); Ishiguro, et al. (2001)). Accumulating evidence from different laboratories suggests that mutant Htt forms aggregates and causes aberrant protein-protein interactions (Bates, G. (2003)). Although a few therapeutic agents with moderate effects have been reported, there is a continuing need in the art for effective treatments for HD.

SUMMARY OF THE INVENTION

Applicants have discovered that certain extracts of *Gastrodia elata* (a traditional Chinese medicinal herb) and related compounds are surprisingly effective in treating conditions such as Huntington's disease and hyperglycemia. For example, administration of extracts of *Gastrodia elata* delayed the progressive deterioration of motor performance and improved the lifespan of a transgenic mouse model for Huntington's disease (Example 2). Also, treatment with the *Gastrodia elata* extract protects cells from apoptosis induced by serum withdrawal (Example 1). Moreover, treatment with the *Gastrodia elata* extract in R6/2 mice reduced elevated blood glucose levels (Example 4) and reduced the formation of mutant Htt aggregates in the liver (Example 5). Further, compounds isolated from these extracts delayed several major symptoms of Huntington's disease (including motor degeneration, body waste, and shortened lifespan) in these mice (Example 6) and prevented apoptosis induced by serum-withdrawal in PC12 cells (Example 5).

In various embodiments, this invention provides a compound represented by the following structural formula:

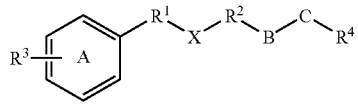

and pharmaceutically acceptable salts and solvates thereof.

Ring A is optionally substituted in addition to $R^3$;

B is an optionally substituted aryl or heteroaryl group;

C is a bond or an optionally substituted cycloaliphatic, heterocyclic, aryl, or heteroaryl group;

$R^1$ and $R^2$ are independently a bond or an optionally substituted alkylene, for example, C1-C4 alkylene;

X is —O—, —S—, —S—S—, —S(O)—, —SO$_2$—, —NR$^a$—, —C(O)NR$^a$—, —NR$^a$C(O)—, —NR$^a$SO$_2$—, or —SO$_2$NR$^a$—;

$R^3$ and $R^4$ are independently —OH, halogen, —CN, —NO$_2$, —OR$^a$, —R$^b$OR$^a$, —C(O)R$^a$, —OC(O)R$^a$, —C(O)OR$^a$, —SR$^a$, —R$^b$SR$^a$, —C(S)R$^a$, —OC(S)R$^a$, —C(S)OR$^a$, —C(O)SR$^a$, —C(S)SR$^a$, —B(OR$^a$)$_2$, —S(O)R$^a$, —SO$_2$R$^a$, —SO$_3$R$^a$, —OSO$_2$R$^a$, —OSO$_3$R$^a$, —PO$_2$R$^a$R$^b$, OPO$_2$R$^a$R$^b$, —PO$_3$R$^a$R$^b$, —OPO$_3$R$^a$R$^b$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$); and $R^a$—$R^d$ are each independently —H or an optionally substituted aliphatic, cycloaliphatic, heterocyclic, benzyl, aryl, or heteroaryl group; or, —N(R$^a$R$^b$), taken together, is an optionally substituted heterocyclic group.

In various embodiments, at least one of $R^1$ and $R^2$ can be an optionally substituted alkylene, e.g., C1-C4 alkylene. In some embodiments, $R^1$ and $R^2$ can each independently be C1-C4 alkylene.

In various embodiments, X can be —NR$^a$—, —C(O)NR$^a$—, —NR$^a$C(O)—, —NR$^a$SO$_2$—, or —SO$_2$NR$^a$—, for example, —NH—. In some embodiments, X can be —O— or —C(O)—. In certain embodiments, X can be —S—, —S(O)—, or —SO$_2$—, for example, —S—.

In various embodiments, $R^3$ and $R^4$ can independently be halogen, —OH, C1-C4 alkanol, —SH, C1-C4 alkanethiol, —CO$_2$H, —NO$_2$, —B(OH)$_2$, —SO$_3$H, —OSO$_3$H, —PO$_3$H$_2$, or —OPO$_3$H$_2$. In some embodiments at least one of $R^3$ and $R^4$ is —OH or —SH. In some embodiments, $R^3$ and $R^4$ can be the same group, for example, —OH.

In various embodiments, Ring B can be optionally substituted phenyl, biphenyl, naphthyl, pyrenyl, anthracyl, imidazolyl, isoimidazolyl, thienyl, furanyl, fluorenyl, pyridyl, pyrimidyl, pyranyl, pyrazolyl, pyrrolyl, pyrazinyl, thiazoyl, isothiazolyl, oxazolyl, isooxazolyl, 1,2,3 triazolyl, 1,2,4 triazolyl, imidazolyl, thienyl, pyrimidinyl, quinazolinyl, indolyl, tetrazolyl, benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl, purinyl or isoindolyl.

In various embodiments, Ring C can be optionally substituted: C3-C8 cycloalkyl; oxazolinyl; thiazolinyl; oxazolidinyl; thiazolidinyl; tetrahydrofuranyl; tetrahydrothiophenyl; morpholino; thiomorpholino; pyrrolidinyl; piperazinyl; piperidinyl; thiazolidinyl; furanose form of glucose, mannose, galactose, allose, altrose, gulose, idose, or talose; or pyranose form of glucose, mannose, galactose, allose, altrose, gulose, idose, or talose.

In various embodiments, the compound can be represented by the following structural formula:

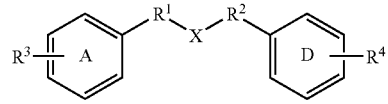

wherein ring D can be optionally substituted or fused to another ring. In some embodiments, the compound can be represented by

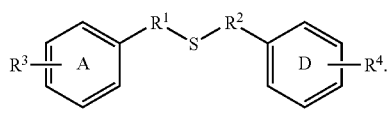

In certain embodiments, the compound can be represented by

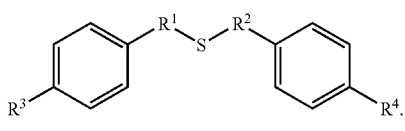

In particular embodiments, the compound can be represented by

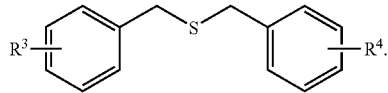

In some embodiments the compound is:

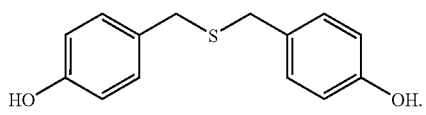

In various embodiments, the compound can be represented by the following structural formula:

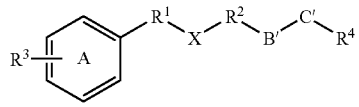

wherein B' is an optionally substituted heteroaryl and C' is an optionally substituted heterocyclic group.

In various embodiments, B' can be an optionally substituted pyrimidyl or purinyl group.

In various embodiments, C', together with R⁴, can be an optionally substituted furanose or pyranose form of glucose, mannose, galactose, allose, altrose, gulose, idose, or talose.

In some embodiments, the compound can be represented by the following structural formula:

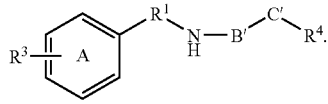

In some embodiments, —NH—B'—C'—R⁴ can be taken together to be an optionally substituted ribonucleoside or deoxyribonucleoside.

In certain embodiments, the compound is:

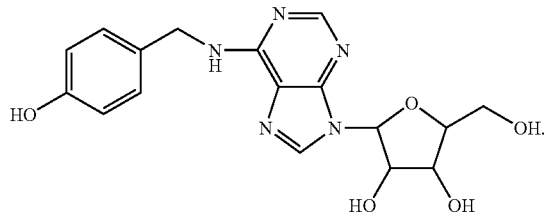

In some embodiments, R¹ and R² are both an optionally substituted alkylene, for example, C1-C4 alkylene.

In some embodiments, X is not —O—. In some embodiments, X is not —S—. In some embodiments, X is not —S—S—. In some embodiments, X is not —S(O)— or —SO₂—. In some embodiments, X is not —NR$^a$—. In some embodiments, X is not —C(O)NR$^a$— or —NR$^a$C(O)—. In some embodiments, X is not —NR$^a$SO₂— or —SO₂NR$^a$—.

In some embodiments, X is —O—. In some embodiments, X is —S—. In some embodiments, X is —S—S—. In some embodiments, X is —S(O)— or —SO₂—. In some embodiments, X is —NR$^a$—. In some embodiments, X is —C(O)NR$^a$— or —NR$^a$C(O)—. In some embodiments, X is —NR$^a$SO₂— or —SO₂NR$^a$—.

In some embodiments, at least one of R³ and R⁴ is —OH.

In some embodiments, R³ and R⁴ are the same.

In some embodiments, at least one of R³ and R⁴ is not halogen. In some embodiments, at least one of R³ and R⁴ is not —OH. In some embodiments, at least one of R³ and R⁴ is not —CN or —NO₂. In some embodiments, at least one of R³ and R⁴ is not —OR$^a$, —R$^b$OR$^a$, —C(O)R$^a$, —OC(O)R$^a$, or —C(O)OR$^a$. In some embodiments, at least one of R³ and R⁴ is not —SR$^a$, —R$^b$SR$^a$, —C(S)R$^a$, —OC(S)R$^a$, —C(S)OR$^a$, —C(O)SR$^a$ or —C(S)SR$^a$. In some embodiments, at least one of R³ and R⁴ is not —B(OR$^a$)₂. In some embodiments, at least one of R³ and R⁴ is not —S(O)R$^a$, —SO₂R$^a$, —SO₃R$^a$, —OSO₂R$^a$ or —OSO₃R$^a$. In some embodiments, at least one of R³ and R⁴ is not —PO₂R$^a$R$^b$, —OPO₂R$^a$R$^b$, —PO₃R$^a$R$^b$ or —OPO₃R$^a$R$^b$. In some embodiments, at least one of R³ and R⁴ is not —N(R$^a$R$^b$), —C(O)N(R$^a$R$^b$), —C(O)NR$^a$NR$^b$SO₂R$^c$, —C(O)NR$^a$SO₂R$^c$ or —C(O)NR$^a$CN. In some embodiments, at least one of R³ and R⁴ is not —SO₂N(R$^a$R$^b$) or —SO₂N(R$^a$R$^b$). In some embodiments, at least one of R³ and R⁴ is not —NR$^c$C(O)R$^a$ or —NR$^c$C(O)OR$^a$).

In some embodiments, at least one of R³ and R⁴ is halogen. In some embodiments, at least one of R³ and R⁴ is —CN or —NO₂. In some embodiments, at least one of R³ and R⁴ is —OR$^a$, —R$^b$OR$^a$, —C(O)R$^a$, —OC(O)R$^a$, or C(O)OR$^a$. In some embodiments, at least one of R³ and R⁴ is —SR$^a$, —R$^b$SR$^a$, —C(S)R$^a$, —OC(S)R$^a$, —C(S)OR$^a$, —C(O)SR$^a$ or —C(S)SR$^a$. In some embodiments, at least one of R³ and R⁴ is —B(OR$^a$)₂. In some embodiments, at least one of R³ and R⁴ is —S(O)R$^a$, —SO₂R$^a$, SO₃R$^a$, OSO₂R$^a$ or —OSO₃R$^a$. In some embodiments, at least one of R³ and R⁴ is —PO₂R$^a$R$^b$, —OPO₂R$^a$R$^b$, —PO₃R$^a$R$^b$ or —OPO₃R$^a$R$^b$. In some embodiments, at least one of R³ and R⁴ is —N(R$^a$R$^b$), —C(O)N(R$^a$R$^b$), —C(O)NR$^a$NR$^b$SO₂R$^c$, —C(O)NR$^a$SO₂R$^c$C or —C(O)NR$^a$CN. In some embodiments, at least one of R³ and R⁴ is —SO₂N(R$^a$R$^b$) or —SO₂N(R$^a$R$^b$). In some embodiments, at least one of R³ and R⁴ is —NR$^c$C(O)R$^a$ or —NR$^c$C(O)OR$^a$).

In some embodiments, the compound is an isolated compound. For example, the compound can be a pure compound, a compound included in a pharmaceutical composition, a compound included in an extract of *Gastrodia* spp. (e.g., *Gastrodia elata*), or the like.

In some embodiments, when R¹ and R² are both methyl, B is phenyl, C is a bond, and R³ and R⁴ are both hydroxyl located para with respect to R¹ and R², X is not —O—, —S—, or —S(O)—. For example, in some embodiments, the compound is not bis(4-hydroxybenzyl)ether, bis(4-hydroxybenzyl)sulfide or bis(4-hydroxybenzyl)sulfoxide.

In some embodiments, the compound is not gastrodin, gastrodioside, or parishin.

Also provided is a pharmaceutically acceptable extract of *Gastrodia* spp. (e.g., *Gastrodia elata*). The extract may be prepared by any method known in the art, such as extraction with organic solvents (e.g., methanol, ethanol, water/ethanol, water/methanol, acetone, methyl ethyl ketone, acetonitrile, and the like). Fractions of these extracts are also provided. The *Gastrodia* may be any species of *Gastrodia*, including, but not limited to, *Gastrodia elata, Gastrodia Cunninghamii, Gastrodia aff. sesamoides, Gastrodia sesamoides*, and the like.

A pharmaceutical composition includes a pharmaceutically acceptable carrier or excipient. In some embodiments, the pharmaceutical composition includes the compound. In some embodiments, the pharmaceutical composition includes the pharmaceutically acceptable extract of *Gastrodia* spp. (e.g., *Gastrodia elata*).

A method of treating a subject having Huntington's disease includes, in various embodiments, administering to the subject an effective amount of the compound and/or the pharmaceutically acceptable extract of *Gastrodia* spp. (e.g., *Gastrodia elata*), or pharmaceutical compositions thereof.

A method of treating a subject having abnormal blood glucose levels includes, in various embodiments, administering to the subject an effective amount of the compound and/or the pharmaceutically acceptable extract of *Gastrodia* spp. (e.g., *Gastrodia elata*), or pharmaceutical compositions thereof. Subjects having abnormal blood glucose levels can exhibit hyperglycemia, and in various embodiments can have one or more diseases such as Huntington's disease, trinucleotide repeat diseases (including SCA1, SCA2, SCA3, SCA6, SCA7, SCA17, dentatorubralpallidoluysian atrophy, spinobulbar muscular atrophy), type I diabetes, type II diabetes, cardiovascular disease, syndrome X, obesity-related hyperglycemia, bulimia-related hyperglycemia, steroid-induced hyperglycemia or the like.

A method of modulating the activity of an $A_{2A}$ receptor in a subject includes, in various embodiments, administering to the subject an effective amount of the compound and/or the pharmaceutically acceptable extract of *Gastrodia* spp. (e.g., *Gastrodia elata*), or pharmaceutical compositions thereof. In some embodiments, the amount of the compound, extract, or pharmaceutical composition administered to the subject is effective to treat the subject for a disease mediated by the $A_{2A}$ receptor, for example, by increasing the activity of the $A_{2A}$ receptor. Such diseases include, for example, chronic heart failure, ischemia peripheral tissues (including liver, kidney and heart), and sepsis.

A method of modulating cyclic adenosine monophosphate levels in a subject includes, in various embodiments, administering to the subject an effective amount of the compound and/or the pharmaceutically acceptable extract of Gastrodia spp. (e.g., Gastrodia elata), or pharmaceutical compositions thereof. In some embodiments, the amount of the compound administered to the subject is effective to increase the level of cyclic adenosine monophosphate in the subject, for example globally or locally in particular cells or tissues. In some embodiments, the amount of the compound, extract, or pharmaceutical composition administered to the subject is effective to treat the subject for a disease mediated by cyclic adenosine monophosphate, for example, by increasing the level of cyclic adenosine monophosphate in the subject. Such diseases include, for example, chronic heart failure, ischemia peripheral tissues (including liver, kidney and heart), and sepsis.

In various embodiments, the pharmaceutical composition includes a pharmaceutically acceptable carrier and the pharmaceutically acceptable water/ethanol extract of Gastrodia spp. or the compound.

Various embodiments include a method of treating a subject with a medical condition, comprising administering to the subject an effective amount of the compound, the extract, or the pharmaceutical composition, e.g., the pharmaceutical composition, wherein the medical condition is Huntington's disease, a trinucleotide repeat disease or abnormal blood glucose levels, or the condition is treatable by modulating $A_{2A}$ receptor activity in the subject or modulating cyclic adenosine monophosphate levels in the subject. In some embodiments, the condition is Huntington's disease, a trinucleotide repeat disease or abnormal blood glucose levels. In some embodiments, the medical condition is Huntington's disease. In some embodiments, the medical condition is hyperglycemia, type I diabetes, type II diabetes, cardiovascular disease, syndrome X, obesity-related hyperglycemia, bulimia-related hyperglycemia, or steroid-induced hyperglycemia. In some embodiments, the medical condition is a trinucleotide repeat disease selected from the group consisting of SCA1, SCA2, SCA3, SCA6, SCA7, SCA17, dentatorubralpallidoluysian atrophy and spinobulbar muscular atrophy. In some embodiments, the condition is selected from the group consisting of chronic heart failure, ischemia of peripheral tissues and sepsis, wherein the compound, the extract, or the pharmaceutical composition is effective to increase the activity of the $A_{2A}$ receptor in the subject or increase cyclic adenosine monophosphate levels in the subject.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

In the drawings:

FIG. 3A is a representative picture of the striatum labeled for ubiquitin in 12-week-old R6/2 mice given the control drinking water from the age of 4 weeks. Scale bar: 25 μm.

FIG. 3C is a bar graph showing the percentage of striatal cells expressing neuronal intranuclear inclusions (NIIs) in 12-week-old R6/2 mice given the control or Gastrodia elata extract (5 mg/mL)-containing drinking water from the age of 4 weeks quantified as described in "Materials and Methods". Scale bar: 25 μm. ** $p<0.01$ when compared to vehicle-treated R6/2 mice at the indicated age, by Student's t-test.

FIG. 5C is a bar graph showing the percentage of liver cells expressing Htt aggregates in 12-week-old R6/2 mice given the control or Gastrodia elata extract (5 mg/mL)-containing drinking water from the age of 4 weeks quantified as described in "Materials and Methods." ** $p<0.01$ when compared to vehicle-treated R6/2 mice at the indicated age, by Student's t-test.

Figure 1:
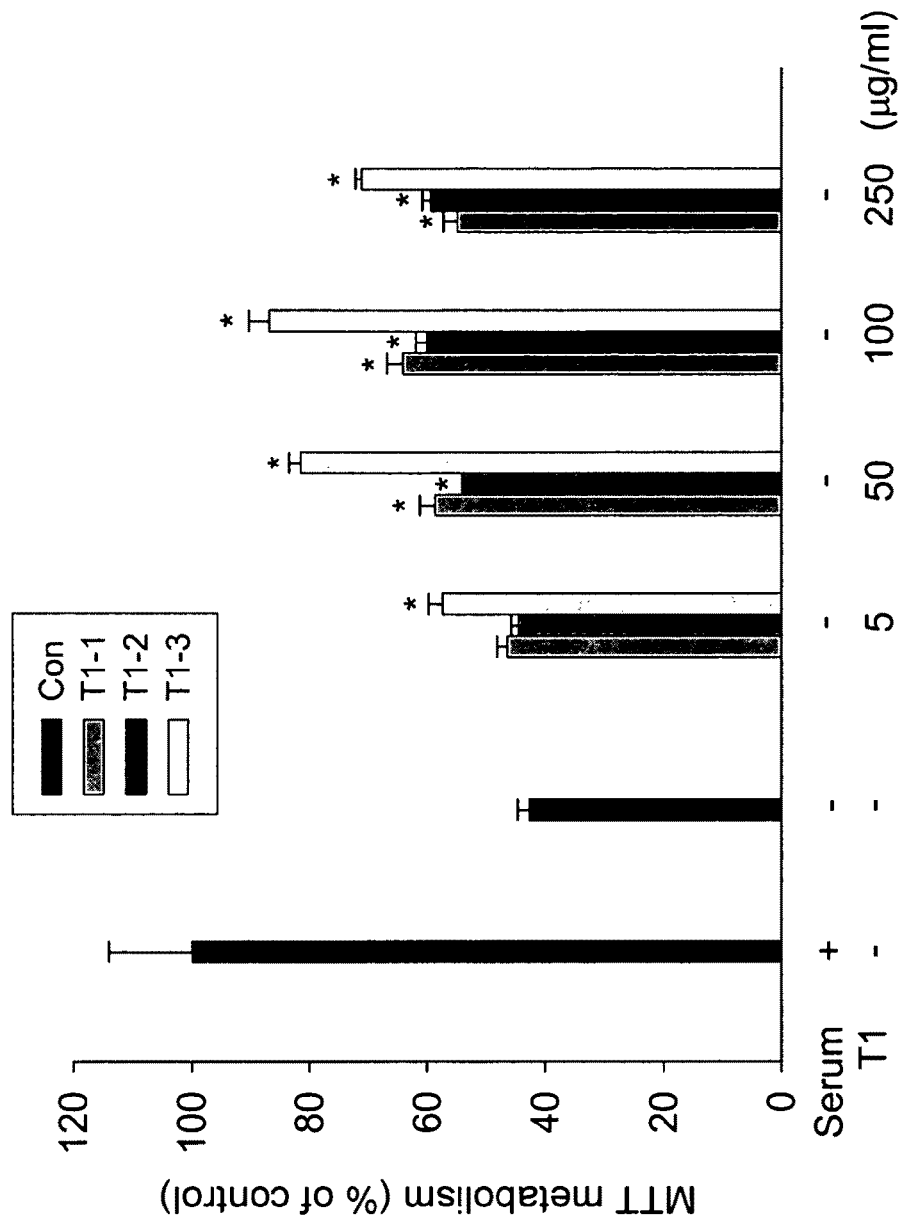
FIG. 1 is a bar graph showing cell viability of PC12 cells expressed as a percentage of the MTT metabolism measured in the serum-containing control group (leftmost bar). A serum deprived group is shown by the second bar from the left. Serum-deprived PC12 cells were treated with differential MeOH extracts (T1-1, T1-2 and T1-3) containing various dosages of the Gastrodia elata extract for 24 h. * $p<0.05$ compared to the serum-deprived group. # $p<0.05$ when compared to the corresponding serum-deprived group.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

*Gastrodia elata* is a Chinese medicinal herb that has been used extensively in Asia for at least 1500 years. It has traditionally been used for the treatment of headaches, dizziness, limb numbness, and spasms and especially convulsive illnesses, such as epilepsy and tetanus. Based on its effective medicinal uses in treating epileptic diseases, many studies were performed to investigate its role in preventing neuronal damage. For example, Gastrodin, a component of *Gastrodia elata*, was shown to alter GABA metabolism in the gerbil hippocampus (An, et al. (2003)). Moreover, an ether fraction of the methanol extracts of *Gastrodia elata* exhibited a protective effect against hippocampal neuronal damage in an ischemic gerbil model and a kainic-acid-treated mouse model (Kim, et al. (2001); Kim, et al. (2003)). An ethyl ether fraction of *Gastrodia elata* also significantly reduced neuronal cell death induced by β-amyloid (Kim, et al. (2003)). Similarly, using a kainic-acid-treated mouse model, Hsieh and colleagues demonstrated that the administration of *Gastrodia elata* extract not only dramatically decreased the counts of convulsive behaviors, but also delayed the onset time as well (Hsieh, et al. (2001)). Such anticonvulsive effects of *Gastrodia elata* appear to be mediated by its free radical-scavenging activities (Hsieh, et al. (2000). In addition, a methanol-extract of *Gastrodia elata* prevented PC12 cells from serum-deprived apoptosis by suppressing the JNK activity (Huang, et al. (2004)). In the present study, we demonstrate that supplementing drinking water with a partial purified extract of *Gastrodia elata* or two novel compounds purified from *Gastrodia elata* markedly ameliorated several major symptoms of HD in the R6/2 transgenic HD mouse model (Mangiarini, et al. (1996)).

Applicants have discovered that certain extracts of *Gastrodia elata* (a traditional Chinese medicinal herb) and related compounds are surprisingly effective in treating conditions such as Huntington's disease and hyperglycemia. For example, administration of extracts of *Gastrodia elata* delayed the progressive deterioration of motor performance and improved the lifespan of a transgenic mouse model for Huntington's disease (Example 2). Also, treatment with the *Gastrodia elata* extract protects cells from apoptosis induced by serum withdrawal (Example 1). Moreover, treatment with the *Gastrodia elata* extract in R6/2 mice reduced elevated blood glucose levels (Example 4)) and reduced the formation of mutant Htt aggregates in the liver (Example 5). Further, compounds isolated from these extracts delayed several major symptoms of Huntington's disease (including motor degeneration, body waste, and shortened life span) in these mice (Example 6) and prevented apoptosis induced by serum-withdrawal in PC12 cells (Example 5).

As used herein, suitable protecting groups which can be employed during synthesis and conditions for protection and deprotection (e.g., for protecting the $R^3$ and $R^4$ groups during synthesis of the compounds) are known in the art and are described, for example, in Greene and Wuts (1991). For example, specific examples of suitable hydroxyl protecting groups include, but are not limited to alkyl ethers (e.g., methyl, ethyl), alkoxy alkyl ethers (e.g., methoxymethyl), silyl ethers (e.g., trimethyl silyl), and the like.

As used herein, "isolated" means that a compound is at least partially purified from a reaction mixture or a biological source, e.g., *Gastrodia elata*. For example, a partially purified or isolated compound can be separated from a reaction mixture or from *Gastrodia elata*, e.g., by one or more steps of extraction, chromatographic separation, crystallization, affinity purification, or other means known to the art. For example, in particular embodiments, the disclosed compounds can be purified by high pressure liquid chromatography.

As used herein, an aliphatic group is a straight chained, branched or cyclic non-aromatic hydrocarbon which is completely saturated or which contains one or more units of unsaturation. An alkyl group is a saturated aliphatic group. Typically, a straight chained or branched aliphatic group has from 1 to about 10 carbon atoms, preferably from 1 to about 4, and a cyclic aliphatic group (for example, the cycloaliphatic groups represented by B and C) has from 3 to about 10 carbon atoms, preferably from 3 to about 8. An aliphatic group is preferably a straight chained or branched alkyl group, e.g., methyl, ethyl, n-propyl, iso-propyl, n-butyl, sec-butyl, tert-butyl, pentyl, hexyl, pentyl or octyl, or a cycloalkyl group with 3 to about 8 carbon atoms. C1-C4 straight chained or branched alkyl or alkoxy groups or a C3-C8 cyclic alkyl or alkoxy group are also referred to as a "lower alkyl" or "lower alkoxy" groups; such groups substituted with —F, —Cl, —Br, or —I are "lower haloalkyl" or "lower haloalkoxy" groups; a "lower hydroxyalkyl" is a lower alkyl substituted with —OH; and the like.

As used herein, an "alkylene group" (for example, the alkylene groups represented by $R^1$ and $R^2$) is a linking alkyl chain represented by —$(CH_2)_n$—, wherein n is an integer from 1-10, preferably 1-4.

As used herein, the term "aryl" (for example, the aryl groups represented by B and C) means C6-C14 carbocyclic aromatic groups such as phenyl, biphenyl, and the like. Aryl groups also include fused polycyclic aromatic ring systems in which a carbocyclic aromatic ring is fused to other aryl, cycloalkyl, or cycloaliphatic rings, such as naphthyl, pyrenyl, anthracyl, and the like.

As used herein, the term "heteroaryl" (for example, the heteroaryl groups represented by B and C) means 5-14 membered heteroaryl groups having 1 or more O, S, or N heteroatoms. Examples of heteroaryl groups include imidazolyl, isoimidazolyl, thienyl, furanyl, fluorenyl, pyridyl, pyrimidyl, pyranyl, pyrazolyl, pyrrolyl, pyrazinyl, thiazoyl, isothiazolyl, oxazolyl, isooxazolyl, 1,2,3-triazolyl, 1,2,4-triazolyl, imidazolyl, thienyl, pyrimidinyl, quinazolinyl, indolyl, tetrazolyl, and the like. Heteroaryl groups also include fused polycyclic aromatic ring systems in which a carbocyclic aromatic ring or heteroaryl ring is fused to one or more other heteroaryl rings. Examples include benzothienyl, benzofuranyl, indolyl, quinolinyl, benzothiazolyl, benzoisothiazolyl, benzooxazolyl, benzoisooxazolyl, benzimidazolyl, quinolinyl, isoquinolinyl, purinyl and isoindolyl. Particular examples of heteroaryl groups include heteroaryl nucleobases such as purinyl derivatives (e.g., 2-amino-1H-purin-6(9H)-one, 6-amino-(9H)purine and the like) and pyrimidiyl derivatives (e.g., 4-aminopyrimidin-2(1H)-one, 5-methylpyrimidine-2,4 (1H,3H)-dione, pyrimidine-2,4(1H,3H)-dione, and the like).

As used herein, non-aromatic heterocyclic groups (for example, the heterocyclic groups represented by B and C) are non-aromatic carbocyclic rings which include one or more heteroatoms such as N, O, or S in the ring. The ring can be five, six, seven or eight-membered. Examples include oxazolinyl, thiazolinyl, oxazolidinyl, thiazolidinyl, tetrahydrofuranyl, tetrahydrothiophenyl, morpholino, thiomorpholino, pyrrolidinyl, piperazinyl, piperidinyl, thiazolidinyl, cyclic saccharides (e.g., glucose, mannose, galactose, allose, altrose, gulose, idose, talose, and the like, in pyranose and furanose forms) and the like.

Suitable optional substituents for a substitutable atom in alkyl, cycloalkyl, aliphatic, cycloaliphatic, heterocyclic, benzylic, aryl, or heteroaryl groups are those substituents that do not substantially interfere with the pharmaceutical activity of the disclosed compounds. A "substitutable atom" is an atom that has one or more valences or charges available to form one or more corresponding covalent or ionic bonds with a substituent. For example, a carbon atom with one valence available (e.g., —C(—H)=) can form a single bond to an alkyl group (e.g., —C(-alkyl)=), a carbon atom with two valences available (e.g., —C(H$_2$)—) can form one or two single bonds to one or two substituents (e.g., —C(alkyl)(H)—, —C(alkyl)(Br)—) or a double bond to one substituent (e.g., —C(=O)—), and the like. Substitutions contemplated herein include only those substitutions that form stable compounds.

For example, suitable optional substituents for substitutable carbon atoms (e.g., the substituents represented by optional substituents for R1, R2, B) include —F, —Cl, —Br, —I, —CN, —NO$_2$, —OR$^a$, —C(O)R$^a$, —OC(O)R$^a$, —C(O)OR$^a$, —SR$^a$, —C(S)R$^a$, —OC(S)R$^a$, —C(S)OR$^a$, —C(O)SR$^a$, —C(S)SR$^a$, —B(OR$^a$)$_2$, —S(O)R$^a$, —SO$_2$R$^a$, —SO$_3$R$^a$, —OSO$_2$R$^a$, OSO$_3$R$^a$, PO$_2$R$^a$R$^b$, OPO$_2$R$^a$R$^b$, —PO$_3$R$^a$R$^b$, —OPO$_3$R$^a$R$^b$, —N(R$^a$R$^b$), —C(O)N(R$^a$R$^b$), —C(O)NR$^a$NR$^b$SO$_2$R$^c$ C1-C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), —C(NR$^c$)—N(R$^a$R$^b$), —NR$^d$—C(NR$^c$)—N(R$^a$R$^b$), —NR$^a$N(R$^a$R$^b$), —CR$^c$=CR$^a$R$^b$, —C=CR$^a$, =O, =S, =CR$^a$R$^b$, =NR$^a$, =NOR$^a$, =NNR$^a$, optionally substituted alkyl, optionally substituted cycloalkyl, optionally substituted aliphatic, optionally substituted cycloaliphatic, optionally substituted heterocyclic, optionally substituted benzyl, optionally substituted aryl, and optionally substituted heteroaryl, wherein R$^a$—R$^d$ are each independently —H or an optionally substituted aliphatic, optionally substituted cycloaliphatic, optionally substituted heterocyclic, optionally substituted benzyl, optionally substituted aryl, or optionally substituted heteroaryl, or, —N(R$^a$R$^b$), taken together, is an optionally substituted heterocyclic group.

Suitable substituents for nitrogen atoms (for example, the nitrogen atoms in groups represented by R$^3$, R$^4$, and X, or ring nitrogen atoms in heteroaryl or heterocyclic groups represented by B and C) having two covalent bonds to other atoms include, for example, optionally substituted alkyl, optionally substituted cycloalkyl, optionally substituted aliphatic, optionally substituted cycloaliphatic, optionally substituted heterocyclic, optionally substituted benzyl, optionally substituted aryl, optionally substituted heteroaryl, —CN, —NO$_2$, —OR$^a$, —C(O)R$^a$, —OC(O)R$^a$, —C(O)OR$^a$, —SR$^a$, —S(O)R$^a$, —SO$_2$R$^a$, —SO$_3$R$^a$, —N(R$^a$R$^b$), —C(O)N(R$^a$R$^b$), —C(O)NR$^a$NR$^b$SO$_2$R$^c$, —C(O)NR$^a$SO$_2$R$^c$, —C(O)NR$^a$CN, —SO$_2$N(R$^a$R$^b$), —SO$_2$N(R$^a$R$^b$), —NR$^c$C(O)R$^a$, —NR$^c$C(O)OR$^a$, —NR$^c$C(O)N(R$^a$R$^b$), and the like.

A nitrogen-containing heteroaryl or non-aromatic heterocycle can be substituted with oxygen to form an N-oxide, e.g., as in a pyridyl N-oxide, piperidyl N-oxide, and the like. For example, in various embodiments, a ring nitrogen atom in a nitrogen-containing heterocyclic or heteroaryl group can be substituted to form an N-oxide.

Also included in the present invention are pharmaceutically acceptable salts of the disclosed compounds. These compounds can have one or more sufficiently acidic protons that can react with a suitable organic or inorganic base to form a base addition salt. For example, when a compound has a hydrogen atom bonded to an oxygen, nitrogen, or sulfur atom, it is contemplated that the compound also includes salts thereof where this hydrogen atom has been reacted with a suitable organic or inorganic base to form a base addition salt. Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Such bases useful in preparing the salts of this invention thus include sodium hydroxide, potassium hydroxide, ammonium hydroxide, potassium carbonate, and the like.

For example, pharmaceutically acceptable salts can include those formed by reaction of the disclosed compounds with one equivalent of a suitable base to form a monovalent salt (i.e., the compound has single negative charge that is balanced by a pharmaceutically acceptable counter cation, e.g., a monovalent cation) or with two equivalents of a suitable base to form a divalent salt (e.g., the compound has a two-electron negative charge that is balanced by two pharmaceutically acceptable counter cations, e.g., two pharmaceutically acceptable monovalent cations or a single pharmaceutically acceptable divalent cation). Examples include Li$^+$, Na$^+$, K$^+$, Mg$^{2+}$, Ca$^{2+}$ and NR$_4$$^+$, wherein each R is independently hydrogen, an optionally substituted aliphatic group (e.g., a hydroxyalkyl group, aminoalkyl group or ammoniumalkyl group) or optionally substituted aryl group, or two R groups, taken together, form an optionally substituted non-aromatic heterocyclic ring optionally fused to an aromatic ring. Generally, the pharmaceutically acceptable cation is Li$^+$, Na$^+$, K$^+$, NH$_3$(C$_2$H$_5$OH)$^+$ or N(CH$_3$)$_3$(C$_2$H$_5$OH)$^+$.

Pharmaceutically acceptable salts of the disclosed compounds with a sufficiently basic group, such as an amine, can be formed by reaction of the disclosed compounds with an organic or inorganic acid to form an acid addition salt. Acids commonly employed to form acid addition salts from compounds with basic groups can include inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

Also included are pharmaceutically acceptable solvates. As used herein, the term "solvate" means a compound of the present invention or a salt thereof that further includes a stoichiometric or non-stoichiometric amount of solvent, e.g., water or organic solvent, bound by non-covalent intermolecular forces.

Also included are pharmaceutical compositions comprising the disclosed compounds. A "pharmaceutical composition" comprises a disclosed compound in conjunction with an acceptable pharmaceutical carrier as part of a pharmaceutical composition for administration to a subject. Formulation of the compound to be administered will vary according to the route of administration selected (e.g., oral (e.g., as a tablet, capsule, lozenge, solution, and the like), intravascular, intraabdominal, intramuscular, subcutaneous, parenteral, buccal, intracranial or cerebrospinal, ocular (e.g., as a solution, ointment, or included in an implant or contact lens), nasal (e.g., as a solution, spray, aerosol, or the like), pharyngeal, pulmonary (e.g., as an aerosol), vaginal, anal, as an implant or depot preparation, in a coating on an implantable medical device, as a topical administration solution, emulsion, capsule, cream, ointment, and the like). Suitable pharmaceutical carriers may contain inert ingredients which do not interact with the compound. Standard pharmaceutical formulation techniques can be employed, such as those described in Remington's Pharmaceutical Sciences (2005). Suitable pharmaceutical carriers for parenteral administration include, for example, sterile water, physiological saline, bacteriostatic saline (saline containing about 0.9% mg/mL benzyl alcohol), phosphate-buffered saline, Hank's solution, Ringer's-lactate and the like. Methods for encapsulating compositions (such as in a coating of hard gelatin or cyclodextrans) are known in the art (Baker, et al. (1986)).

It will also be understood that certain of the disclosed compounds can be obtained as different stereoisomers (e.g., diastereomers and enantiomers) and that the invention includes all isomeric forms and racemic mixtures of the disclosed compounds and methods of treating a subject with both pure isomers and mixtures thereof, including racemic mixtures. Stereoisomers can be separated and isolated using any suitable method, such as chromatography.

A method of treating a subject having Huntington's disease includes, in various embodiments, administering to the subject an effective amount of the compound and/or the pharmaceutically acceptable extract of *Gastrodia* spp. (e.g., *Gastrodia elata*), or pharmaceutical compositions thereof.

A method of treating a subject having abnormal blood glucose levels includes, in various embodiments, administering to the subject an effective amount of the compound and/or the pharmaceutically acceptable extract of *Gastrodia* spp. (e.g., *Gastrodia elata*), or pharmaceutical compositions thereof. Subjects having abnormal blood glucose levels can exhibit hyperglycemia, and in various embodiments can have one or more diseases such as Huntington's disease, type I diabetes, type II diabetes, cardiovascular disease, syndrome X, obesity-related hyperglycemia, bulimia-related hyperglycemia, steroid-induced hyperglycemia or the like.

A method of modulating the activity of an $A_{2A}$ receptor in a subject includes, in various embodiments, administering to the subject an effective amount of the compound and/or the pharmaceutically acceptable extract of *Gastrodia* spp. (e.g., *Gastrodia elata*), or pharmaceutical compositions thereof. In some embodiments, the amount of the compound, extract, or pharmaceutical composition administered to the subject is effective to treat the subject for a disease mediated by the $A_{2A}$ receptor, for example, by increasing the activity of the $A_{2A}$ receptor.

A method of modulating cyclic adenosine monophosphate levels in a subject includes, in various embodiments, administering to the subject an effective amount of the compound and/or the pharmaceutically acceptable extract of *Gastrodia* spp. (e.g., *Gastrodia elata*), or pharmaceutical compositions thereof. In some embodiments, the amount of the compound administered to the subject is effective to increase the level of cyclic adenosine monophosphate in the subject, for example globally or locally in particular cells or tissues. In some embodiments, the amount of the compound, extract, or pharmaceutical composition administered to the subject is effective to treat the subject for a disease by cyclic adenosine monophosphate, for example, by increasing the level of cyclic adenosine monophosphate in the subject.

EXAMPLES

Materials and Methods

Preparation of a *Gastrodia Elata* Extract

The rhizome of *Gastrodia elata* Bl. was purchased from a local herbal store in Taipei. Slices of *Gastrodia elata* were extracted by aqueous ethanol overnight (60° C.). The crude extract was concentrated using a vacuum rotary evaporator under reduced pressure. The dried sample was subjected to ion column chromatography (DIAION® HP20, HP21, Mitsubishi Chemical, Tokyo, Japan) and eluted using a $H_2O$ to MeOH gradient. Fractions were screened for activity to protect PC12 cells from apoptosis induced by serum-withdrawal. Fractions identified as having such activity were combined and purified on a SEPHADEX® LH-20 column (Pharmacia LKB, Biotechnology AB, Uppsala Sweden). Repeatedly eluted with MeOH yielded two active components designated T1-C and T1-11. High-pressure liquid chromatography using a Merck PUROSPHER® RP-18e (Merck KGaA Life Science & Analytics, Darmstadt, Germany), (250×4.6 mm) column, a UV 270-nm detector, a mobile phase gradient from 70% to 40% $H_2O$/MeOH for 40 min, and from 40% to 20% $H_2O$/MeOH for 5 min, at a flow rate of 0.5 mL/min, was used to monitor the chemical profiles of different batches.

Cell Culture

PC12 cells purchased from American Type Culture Collection (ATCC, Manassas, Va., USA) were maintained in Dulbecco's Modified Eagle Medium (DMEM) supplemented with 10% horse serum and 5% fetal bovine serum and incubated in a $CO_2$ incubator (5%) at 37° C. The striatal progenitor cell line (ST14A) was obtained from Dr. E. Cattaneo (University of Milano, Italy) and was maintained in an incubation chamber with 10% $CO_2$-90% air at 33° C. as described previously (Ehrlich, et al. (2001)).

MTT Assay

PC12 cells were serum-deprived by three washes of phosphate buffered saline (PBS) and resuspended in DMEM. The suspended cells were plated on 96-well plates ($1 \times 10^4$ cells/well) and treated with the indicated reagent(s). After treatment for 21 h, 3-(4,5-dimethylthiazol-2-yl)-2,5-diphenyl tetrazolium bromide (MTT) was added to the medium (0.5 mg/mL) and incubated at 37° C. for another 3 h. After discarding the medium, 100 µl dimethyl sulfoxide (DMSO) was then applied to each well to dissolve the formazan crystals and the absorbances at 570 and 630 nm in each well were measured on a micro-enzyme linked immunosorbent assay (ELISA) reader.

Animals and Drug Administration:

Male R6/2 mice and littermate controls were mated to female control mice (B6CBAFI/J). Mice were obtained from Jackson Laboratories, Bar Harbor, Me., USA. Offspring were identified by the PCR genotyping technique of genomic DNA extracted from tail tissues using primers located in the transgene (5'-CCGCTCAGGTTCTGCTTTTA-3' (SEQ ID NO: 1) and 5'-GGCTGAGGAAGCTGAGGAG-3' (SEQ ID NO: 2)) to ensure that the number of CAG repeats remained approximately 150. In total, 67 R6/2 transgenic mice were used in this study. Animals were housed at the Institute of Biomedical Sciences Animal Care Facility under a 12-h light/dark cycle. Daily injections of the indicated reagent were given between 13:00 and 18:00. Body weights of mice were recorded once daily, prior to diet administration. Animal experiments were performed under protocols approved by the Academia Sinica Institutional Animal Care and Utilization Committee, Taiwan.

Rotarod Performance:

Motor coordination was assessed using a rotarod apparatus (UGO BASILE, Comerio, Italy) at a constant speed (12 rpm) over the period of 2 min (Carter, et al. (1999)). All mice were trained for 2 days at the age of 6 weeks to allow them to become acquainted with the rotarod apparatus. Animals were then tested three times per week from the ages of 7 to 12 weeks. For each test, animals were placed in the apparatus before initiation of rotation. Latency to falling was automatically recorded. Each mouse was given three trials for a maximum of 2 min for each trial.

Figure 3B:
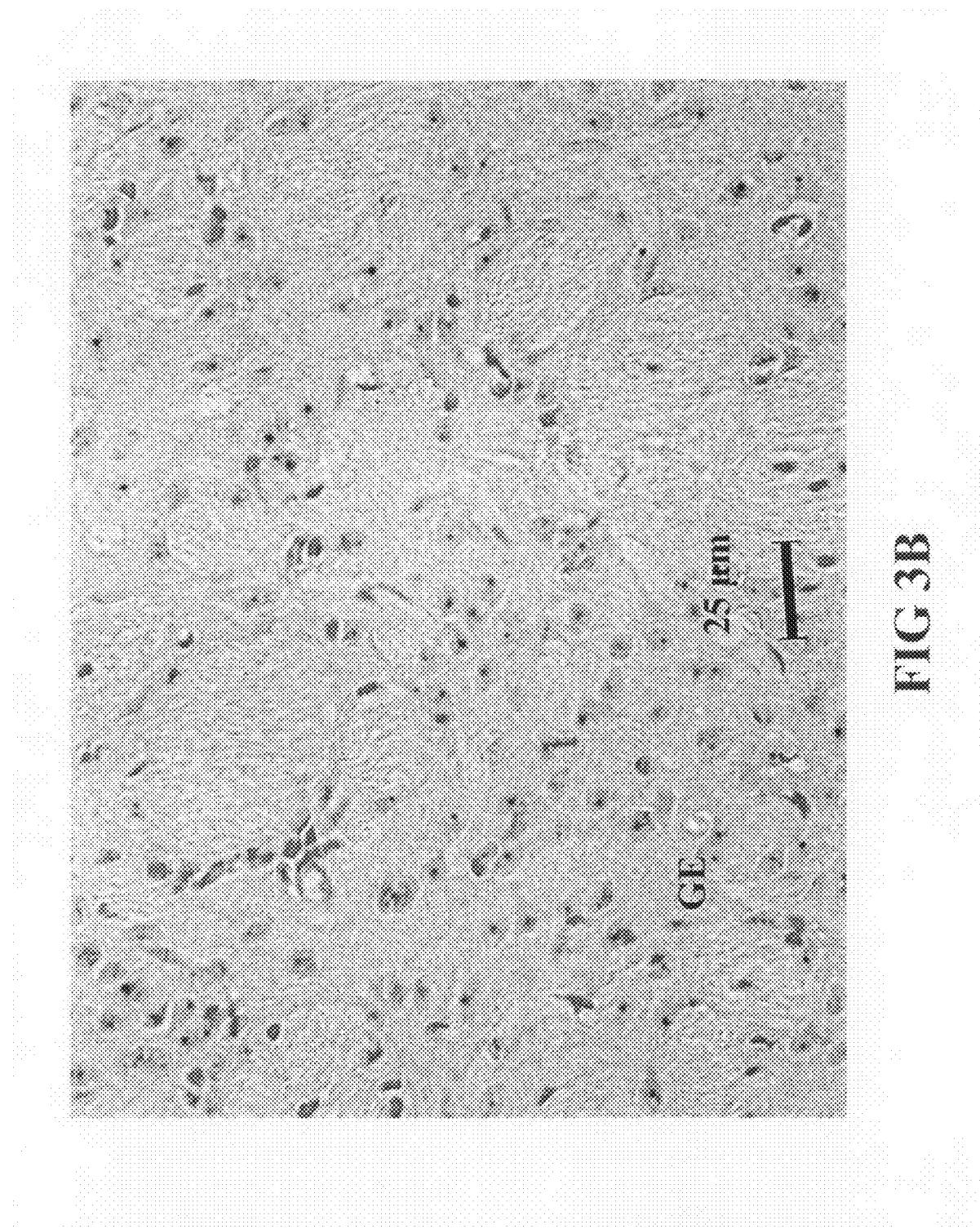
FIG. 3B is a representative picture of the striatum labeled for ubiquitin in 12-week-old R6/2 mice given Gastrodia elata extract (5 mg/mL)-containing drinking water from the age of 4 weeks. Scale bar: 25 μm.

Immunohistochemistry and Quantitation:

Brain sections (30 µm) containing the striatum (interaural 5.34 mm/bregma 1.54 mm to interaural 3.7 mm/bregma −0.1 mm) and liver sections (20 µm) were used in the immunohistochemical analyses. Single antigen immunostaining was carried out using the avidin-biotin-peroxidase complex (ABC) method as previously described (Wu, et al. (1998)). In general, a 1:2000 dilution was used for the polyclonal anti-ubiquitin antiserum (DakoCytomation Denmark A/S, Glostrup, Denmark). Three different sections labeled with the anti-ubiquitin antiserum and counterstained with methyl green from one brain were quantified. In total, six mice of each treatment at 12 weeks of age were analyzed. At least 1200 and 300 cells from each mouse were counted to determine the percentage of striatal cells and liver cells expressing ubiquitinized Htt aggregates, respectively. FIG. 3A is a representative picture of the striatum labeled for ubiquitin in 12-week-old R6/2 mice given the control drinking water from the age of 4 weeks. Scale bar: 25 µm. FIG. 3B is a representative picture of the striatum labeled for ubiquitin in 12-week-old R6/2 mice given *Gastrodia elata* extract (5 mg/mL)-containing drinking water from the age of 4 weeks. Scale bar: 25 µm. FIG. 3C is a bar graph showing the percentage of striatal cells expressing neuronal intranuclear inclusions (NIIs) in 12-week-old R6/2 mice given the control or *Gastrodia elata* extract (5 mg/mL)-containing drinking water from the age of 4 weeks quantified as described in "Materials and Methods". Scale bar: 25 µm. ** $p<0.01$ when compared to vehicle-treated R6/2 mice at the indicated age, by Student's t-test.

Measurements of Blood Glucose Level:

Mice were decapitated, and blood samples (1~1.5 mL) were collected from each mouse into ethylene tetraamine diacetate (EDTA)-blood tubes. Blood glucose concentrations were measured using an ABBOTT Alcyon 300i analyzer (ABBOTT Labs, Abbott Park, Ill., USA).

Tandem Mass Spectrometric Screening of Blood Amino Acids:

Sample collections were performed by impregnating filter papers (S&S 903; Schleicher & Shuell, Dassel, Germany) with blood (25 µl) from the tail vein of R/2 mice at age of 10.5 weeks. Before the analyses, blood was eluted from the filter paper, and the levels of amino acids were determine using a tandem mass spectrometer (Quattro Micro; Micromass, Beverly, Mass., USA) as described previously (Wu, et al. (2004)).

Example 1

Treatment with *Gastrodia elata* Extract Protects Cells from Apoptosis Induced by Serum Withdrawal We previously found that an $A_{2A}$-R-specific agonist specifically ameliorates several major symptoms of HD (Chou, et al. (2005)). In addition, a *Gastrodia elata* extract has been shown to prevent serum-induced apoptosis of PC12 cells, as well as $A_{2A}$-R activation (Huang, et al. (2004)). In the present study, we first performed partial purification of different fractions of *Gastrodia elata* as described in "Methods". The aqueous ethanolic extract of *Gastrodia elata*, which was then subjected to DIAION® HP-20 column chromatography and eluted using a $H_2O$ to MeOH gradient. As shown in FIG. 1, several fractions of the methanol extraction (T1-1, T1-2 and T1-3) displayed activities to protect PC 2 cells from apoptosis induced by serum withdrawal. The most effective fraction was the T1-3 fraction.

Example 2

Figure 2A:
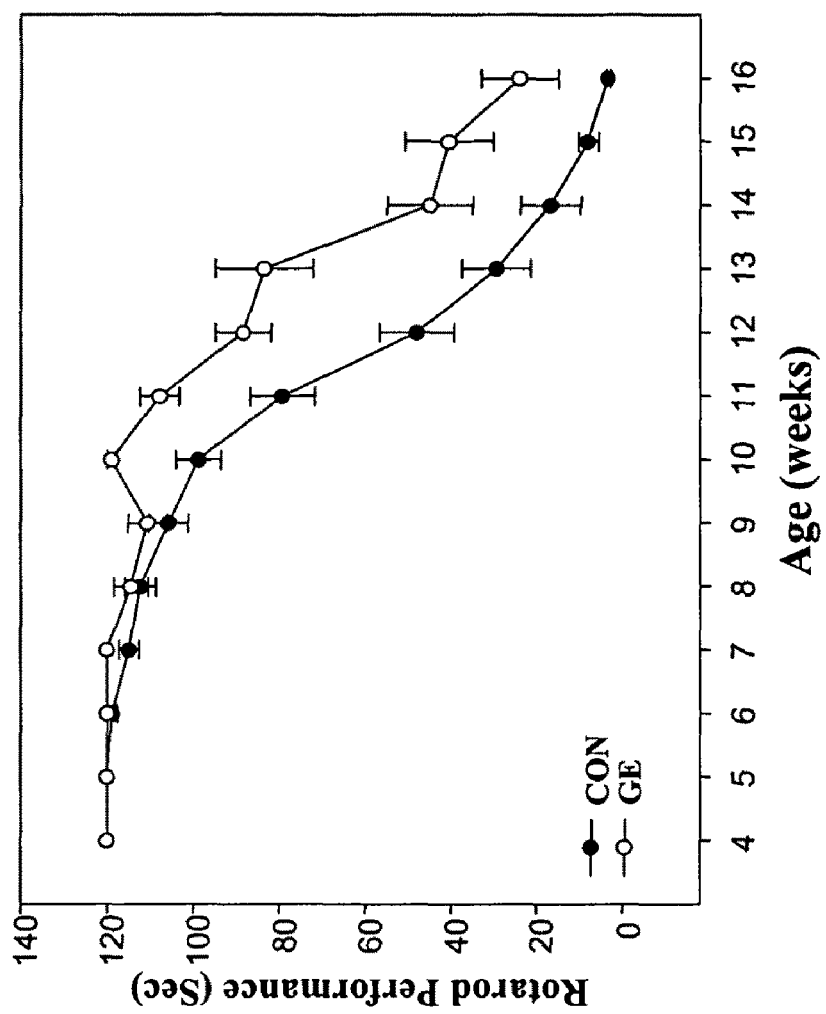
FIG. 2A is a graph of rotarod performance in seconds versus age in R6/2 mice given the control (CON, n=11) or Gastrodia elata extract (5 mg/mL, n=12)-containing drinking water from the age of 4 weeks.
Figure 2B:
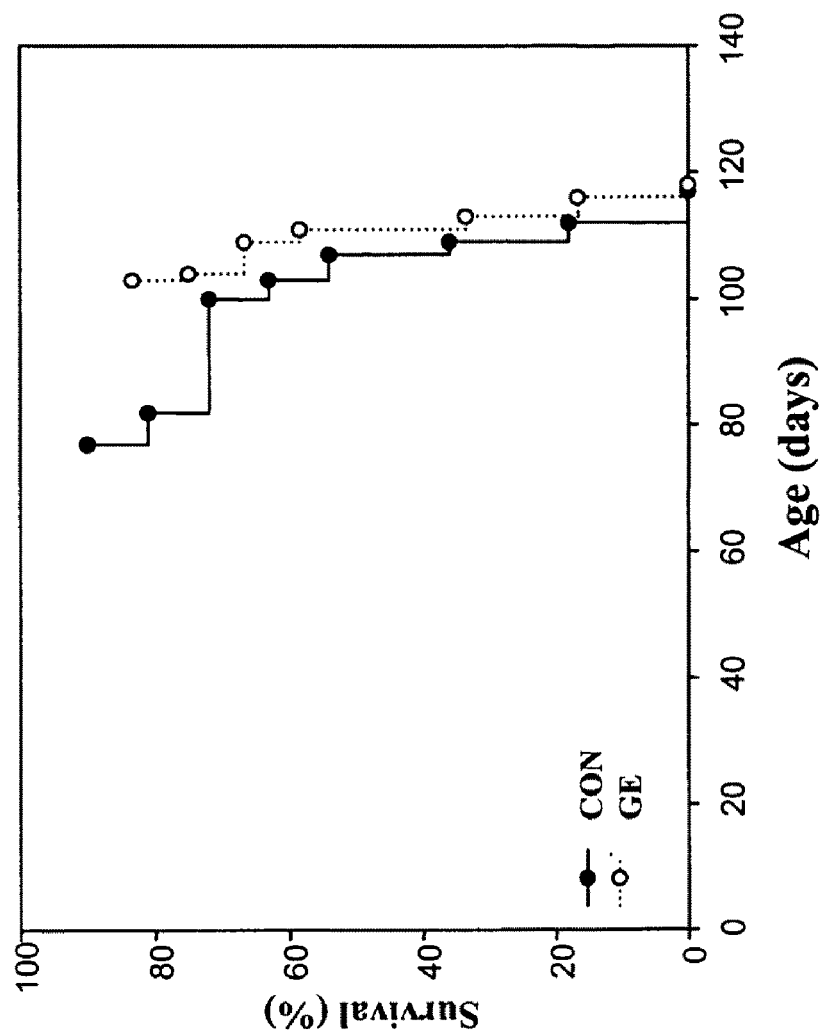
FIG. 2B is a graph of survival percentage versus age in R6/2 mice given the control (CON, n=11) or Gastrodia elata extract (5 mg/mL, n=12)-containing drinking water from the age of 4 weeks.

Treatment with *Gastrodia elata* Extract Improves Motor Coordination and Lifespan in R6/2 Mice The therapeutic effect of the T1-3 fractions on R6/2 mice was examined. Mice were treated with the T1-3 fractions (added to drinking water 5 mg/mL) beginning at the age of 4 weeks for up to 12 weeks. As shown in FIG. 2A, the ability of R6/2 HD mice to complete a full course (120 s) of the rotarod test decreased from the age of 10 weeks. Supplementation of the T1-3 fractions in the drinking water attenuated the progressive deterioration in motor coordination in R6/2 mice as measured by rotarod performance. FIG. 2B shows that the lifespan of R6/2 mice was moderately improved by chronic T1-3 fraction treatment. No effects on general animal behaviors or performance were observed that would suggest toxicity of the T1-3 fractions employed in this study.

Example 3

Treatment with *Gastrodia elata* Extract Reduces Neuronal Intranuclear Inclusions in R6/2 Mice The T1-3 fractions were examined for the effect on the formation of neuronal intranuclear inclusions (NIIs). Since NIIs observed in the brains of R6/2 mice were all ubiquitinated (Meade, et al. (2002)), brain sections of R6/2 mice treated with chronic T1-3 treatment at the age of 12 weeks were stained with an anti-ubiquitin antibody followed by counterstaining with methyl green. FIGS. 3A-C show that T1-3 supplement significantly reduced the percentage of striatal cells expressing NIIs in R6/2 mice, suggesting that *Gastrodia elata* treatment delayed the development of NIIs in HD mice. No NII was found in the brains of wildtype mice (Chou, et al. (2005) J Neurochem 93, 310-20).

Example 4

Figure 4:
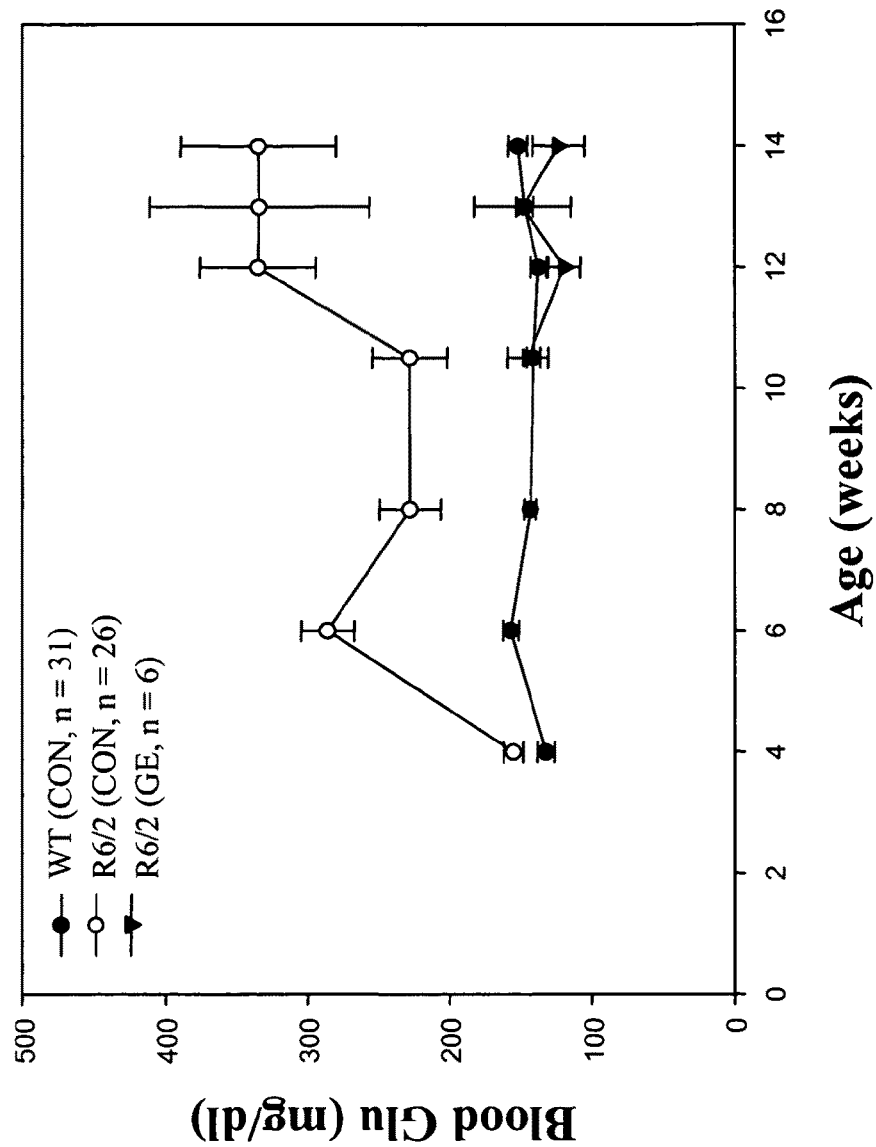
FIG. 4 is a graph of blood glucose in mg/dl versus age in wildtype control mice, R6/2 control mice, and R6/2 mice given the Gastrodia elata extract (5 mg/mL)-containing drinking water from the age of 4 weeks. Blood samples were collected at the indicated age to determine blood glucose as described in "Methods".

Treatment with *Gastrodia elata* Extract Reduces Elevated Blood Glucose in R6/2 Mice Studies from various laboratories including ours have demonstrated that both HD patients and HD mice exhibit hyperglycemia (Chou, et al. (2005); Podolsky, et al. (1972); Duan, et al. (2003)). Because suppression of hyperglycemia has been associated with improvements in neurological deficits of HD subjects (Duan et al.), we examined whether chronic T1-3 supplementation normalized the blood glucose levels in R6/2 mice. Consistent with an earlier report (Hurlbert, et al. (1999)), an approximately 1-fold increase in the levels of blood glucose was found in R6/2 mice from the age of 6 weeks when compared with wildtype mice. The enhanced blood glucose level was much more significant in the late stage of HD when impaired locomotor coordination was observed (FIG. 2A). FIG. 4 shows that treatment with the T1-3 fraction reduced the aberrantly elevated blood glucose in R6/2 mice, demonstrating improved glucose regulation and energy metabolism by the T1-3 fractions.

TABLE 1

Blood levels of amino acids in R6/2 mice compared to wildtype mice

| Blood component | WT (CON) N = 20 | R6/2 (CON) N = 24 | R6/2 (RG) N = 14 |
|---|---|---|---|
| Arg | 31.30 ± 3.24** | 78.60 ± 6.41 | 49.87 ± 9.96 |
| Ala | 258.39 ± 25.76* | 383.30 ± 24.23 | 303.75 ± 54.31 |
| Cit | 22.51 ± 3.46* | 41.38 ± 4.79 | 37.49 ± 8.70 |
| Orn | 12.02 ± 2.05* | 24.25 ± 5.02 | 27.88 ± 4.99 |
| Gln | 253.92 ± 29.10* | 471.71 ± 70.86 | 570.44 ± 110.31 |
| Glu | 153.24 ± 15.22* | 230.80 ± 17.18 | 164.92 ± 28.22* |
| Gly | 187.99 ± 14.54* | 309.86 ± 20.52 | 274.04 ± 45.02 |
| His | 4.23 ± 0.66 | 3.27 ± 0.38 | 3.36 ± 0.64 |
| Met | 13.79 ± 1.33* | 28.55 ± 1.79 | 26.92 ± 5.04 |
| Phe | 75.09 ± 6.63* | 97.28 ± 3.03 | 70.40 ± 10.03* |
| Pro | 738.22 ± 99.42 | 812.81 ± 52.68 | 546.90 ± 87.47* |
| Ser | 30.87 ± 2.75** | 60.31 ± 3.60 | 41.20 ± 4.62** |
| Thr | 65.38 ± 7.00 | 74.07 ± 5.27 | 53.45 ± 6.77* |
| Trp | 32.65 ± 3.18* | 46.49 ± 4.35 | 31.46 ± 5.68* |
| Tyr | 47.09 ± 4.12** | 75.82 ± 4.82 | 48.85 ± 7.01** |
| Val | 153.54 ± 16.43 | 192.61 ± 13.99 | 131.33 ± 20.17* |
| Asp | 72.81 ± 23.06 | 54.95 ± 6.99 | 141.04 ± 26.00* |

Example 5

Figure 5A:
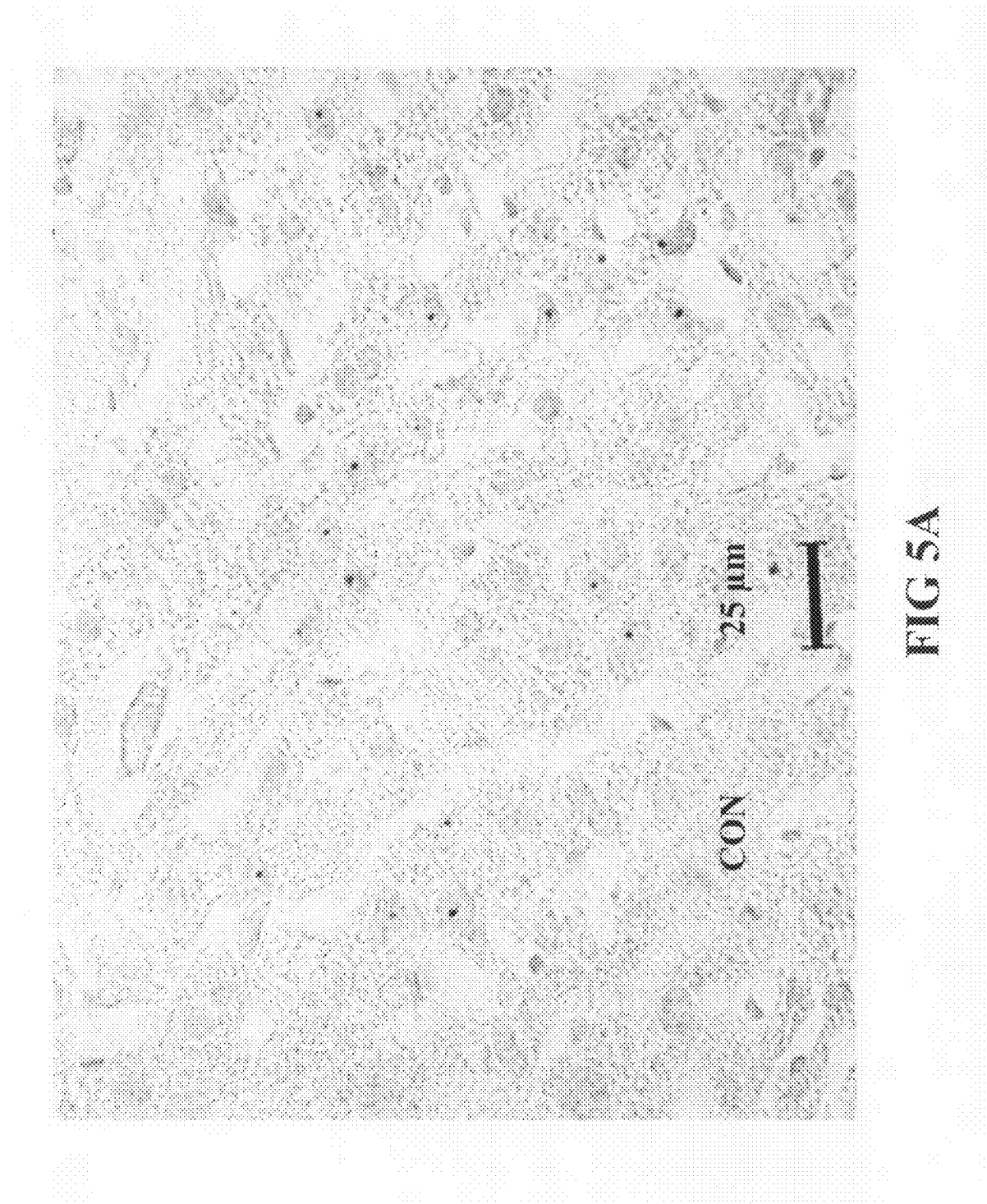
FIG. 5A is a representative picture of the liver labeled for ubiquitin in 12-week-old R6/2 mice given the control drinking water from the age of 4 weeks. Scale bar: 25 μm.
Figure 5B:
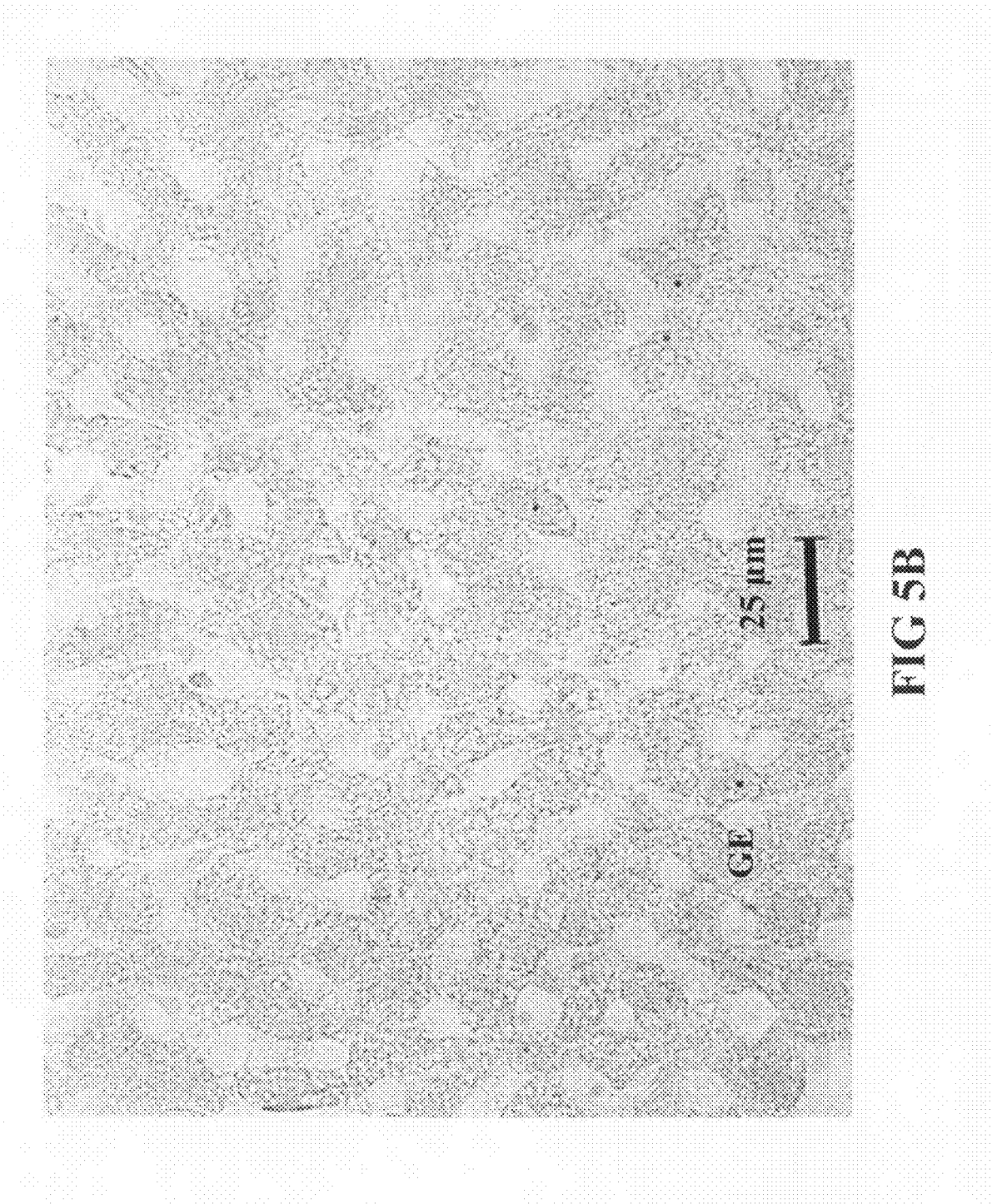
FIG. 5B is a representative picture of the liver labeled for ubiquitin in 12-week-old R6/2 mice given the Gastrodia elata extract (5 mg/mL)-containing drinking water from the age of 4 weeks. Scale bar: 25 μm.

Treatment with *Gastrodia elata* Extract Reduces Htt Aggregates in the Liver of HD Mice Since metabolic abnormalities might contribute to the pathology of HD, we further determined the level of blood amino acids. As shown in Table 1, 12 of the 17 amino acids examined were markedly higher in the blood of R6/2 mice when compared to those of the wildtype mice. The T1-3 fraction supplementation normalized seven of the elevated amino acid levels in R6/2 mice. Since abnormal amino acid metabolism might be caused by liver dysfunction (Holm, et al. (1999)), we investigated the formation of Htt aggregates in the liver. Consistent with previous reports (Tanaka, et al. 2004), Htt aggregates could be observed in the liver of R6/2 mice (FIG. 5A). Chronic supplementation reduced the Htt aggregates in the liver of HD mice (FIG. 5B). This protective effect is consistent with the neuroprotective effect of *Gastrodia elata* previously implied in ischemia-induced neuronal damage and Alzheimer's disease (Kim, et al. (2001); Kim, et al. (2003) Phytother Res; Kim, et al. (2003) J Ethnopharmacol; Hsieh, et al. (2001)).

Example 6

Figure 6:
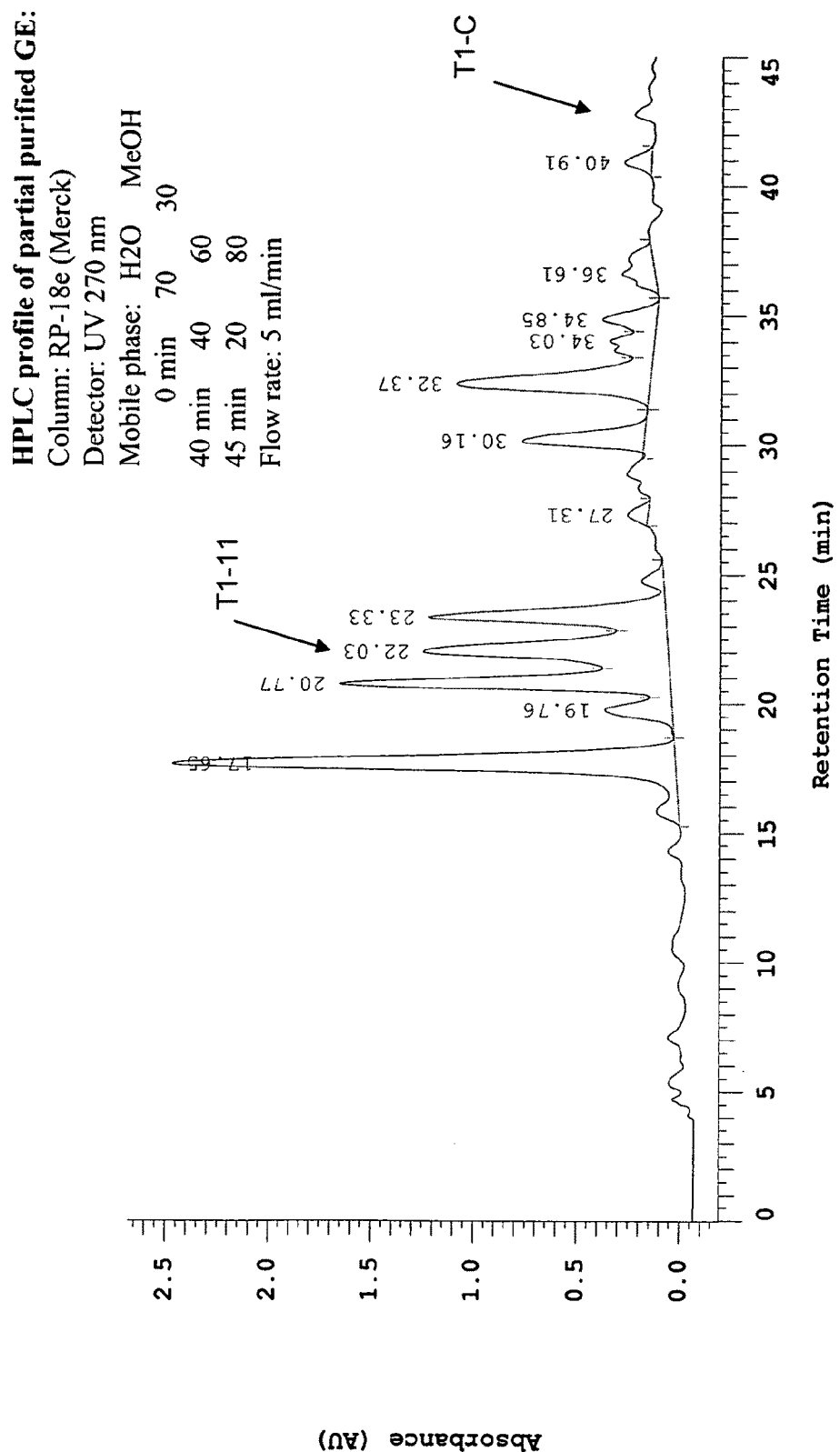
FIG. 6 is a chromatogram of active fractions of Gastrodia elata. HPLC conditions included a Merck RP-18e (250×4.6 mm) column, the gradient of the mobile phase was from 70% to 40% $H_2O$/MeOH for 40 min and from 40% to 20$H_2O$/MeOH for 5 min at a flow rate of 0.5 mL/min and a detection wavelength of 270 nm. The positions of the two active components (T1-C and T1-11) are marked with arrows.
Figure 7A:
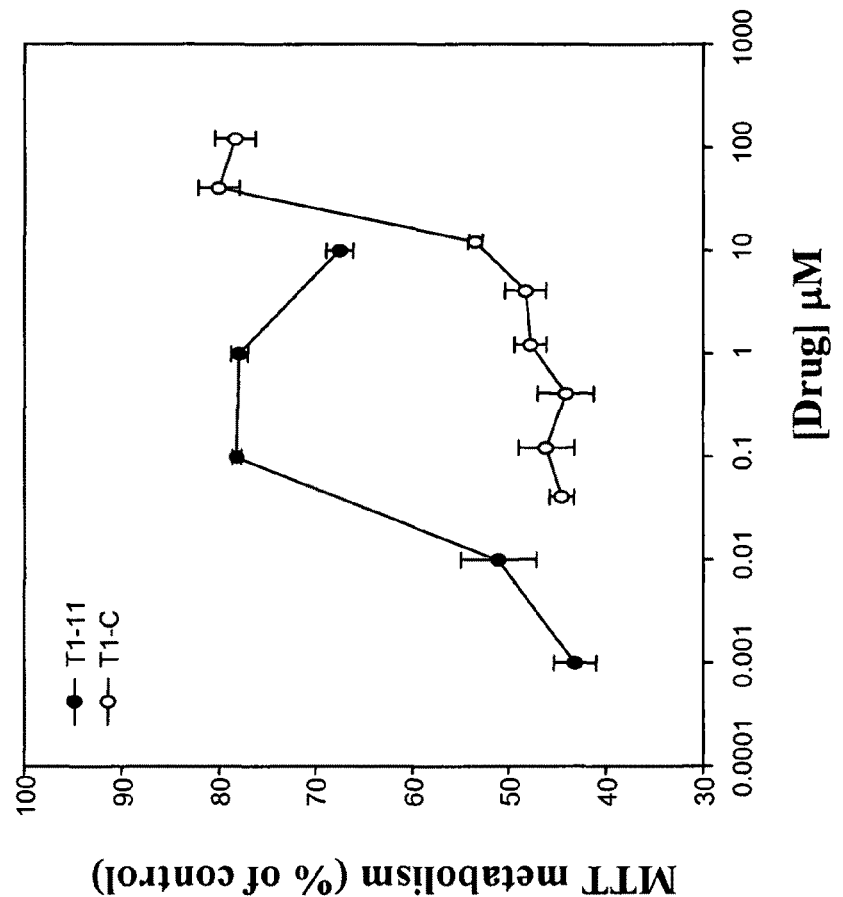
FIG. 7A is a graph showing cell viability of T1-C or T1-11 treated serum deprived PC12 cells expressed as a percentage of the MTT metabolism of control PC12 cells. Serum-deprived PC12 cells were treated with or without the indicated drug at the desired dose for 24 h. Cell viability was monitored by the MTT assay, and is expressed as a percentage of the MTT activity measured in the serum-containing group. Data points represent the mean±SEM of at least three independent experiments (n=3~6).
Figure 7B:
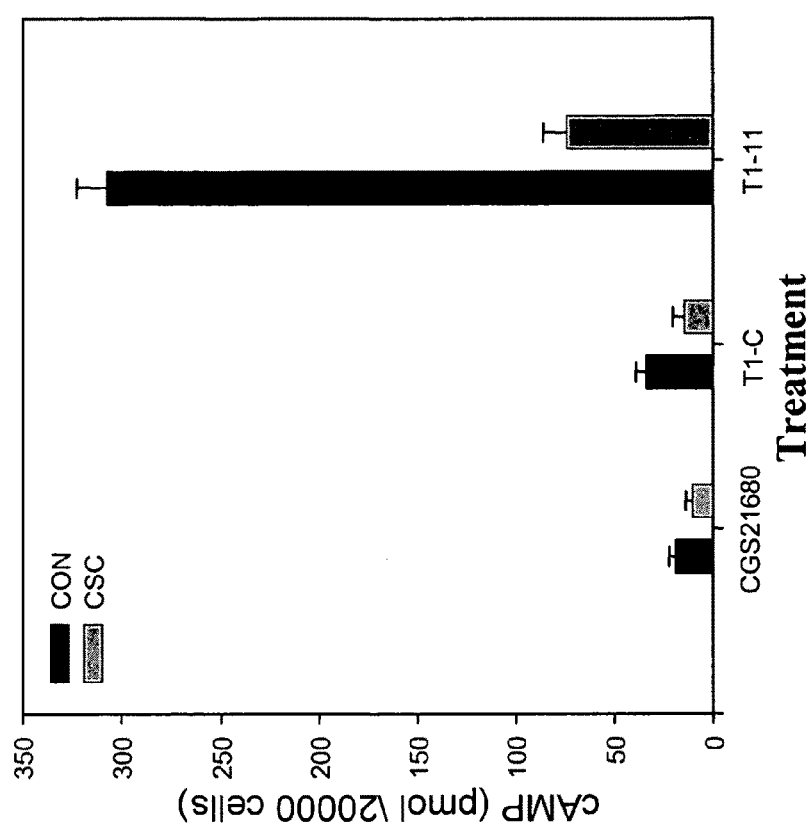
FIG. 7B is a bar graph showing cellular cAMP content of control ST14A cells and ST14A cells treated with CGS21680 (CGS, 10 μM), T1-C (10 μM), or T1-11 (26.8 μM) for 20 min at RT. The cellular cAMP content was measured as described.

Isolated Components of Active *Gastrodia elata* Extracts Protect PC12 Cells from Apoptosis and May Function as Agonists of the $A_{2A}$-R The active T1-3 fractions were combined and subjected to fractionation and purification utilizing Sephadex LH-20 column chromatography (FIG. 6). Fourteen known compounds (including gastrodin, parishin, 4-hydroxybenzyl alcohol, 4,4'-dihydroxybenzyl sulfoxide, 4-hydroxyphenylmethane, bis(4-hydroxybenzyl)ether, 4-hydroxybenzyl ethyl ether, 4-hydroxybenzyl methyl ether, trimethylcitrate, 4-hydroxybenzaldehyde, uridine, adenosine, 5-(hydroxymethyl)-2-furaldehyde and T1-C (Taguchi, et al. (1981); Lin, et al. (1996) Phytochemistry 42, 549-551; Hayashi, et al. (2002); Huang, et al. (2005), Xiao, et al. (2002)), and a previously uncharacterized component (T1-11) were identified. Abilities of these isolated fractions to prevent apoptosis induced by serum withdrawal were tested. Out of the 15 compounds, two components (T1-C and T1-11) were active in protecting PC12 cells from apoptosis (FIG. 7A). T1-C and T1-11 comprise approximately 5% and 0.2% of the T1-3 fraction, respectively. Although being a relatively minor component, T1-11 is much more potent than T1-C in protecting PC12 cells from apoptosis. Interestingly, treating ST14A cells (Ehrlich, et al. (2001)) with either T1-C or T1-11 also elevated the intracellular cAMP level as did an $A_{2A}$-R selective agonist, CGS21680. In addition, the cAMP response could be suppressed by an $A_{2A}$-R-dependent antagonist (CSC, FIG. 7B). Thus, it is believed that T1-C and T1-11 can function as agonists of the $A_{2A}$-R.

Example 7

Figure 8A:
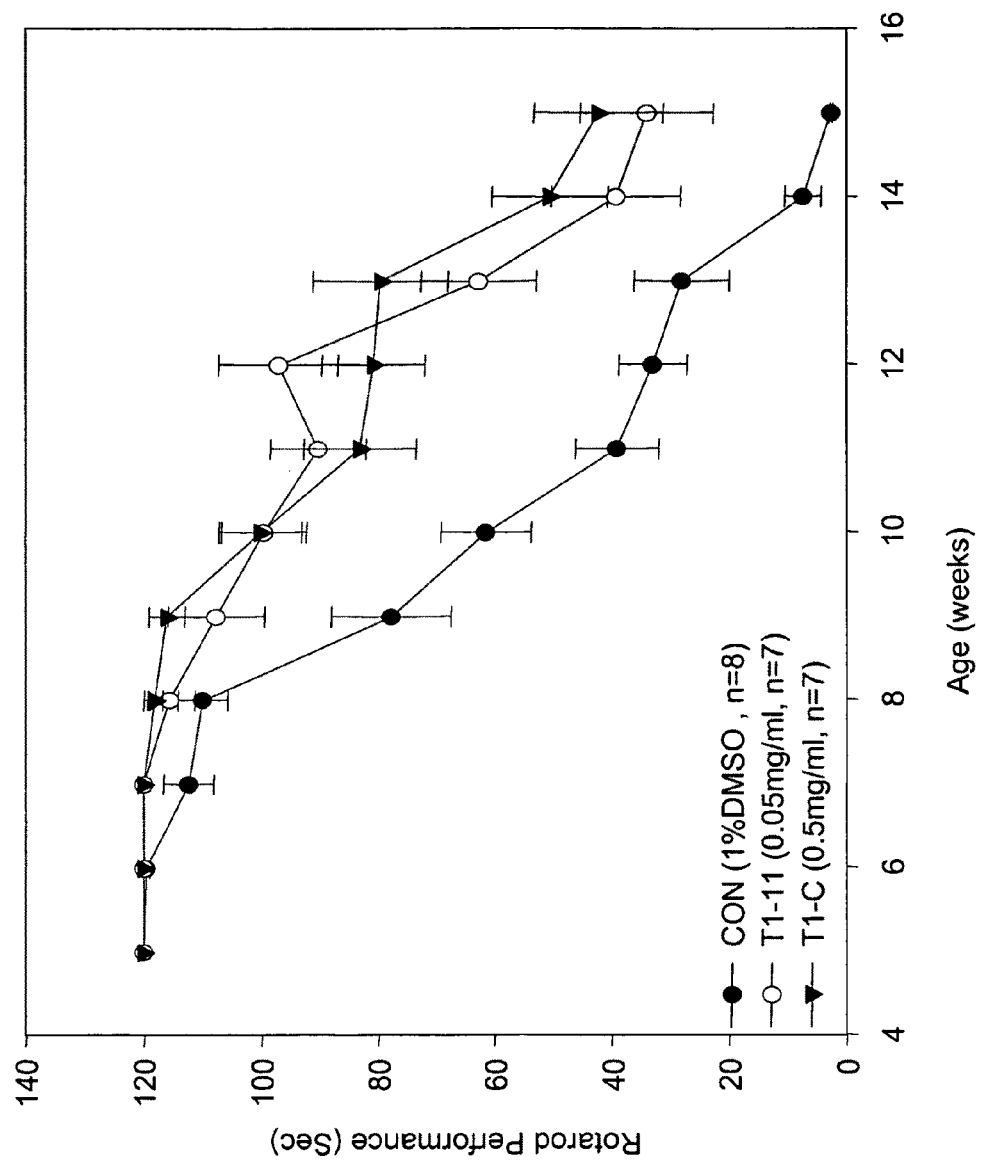
FIG. 8A is a graph showing rotarod performance in R6/2 mice were given the control (CON, 1% DMSO, n=8), T1-C (0.5 mg/mL in 1% DMSO, n=7) or T1-11 (0.05 mg/mL in 1% DMSO, n=8)-containing drinking water from the age of 4 weeks.
Figure 8B:
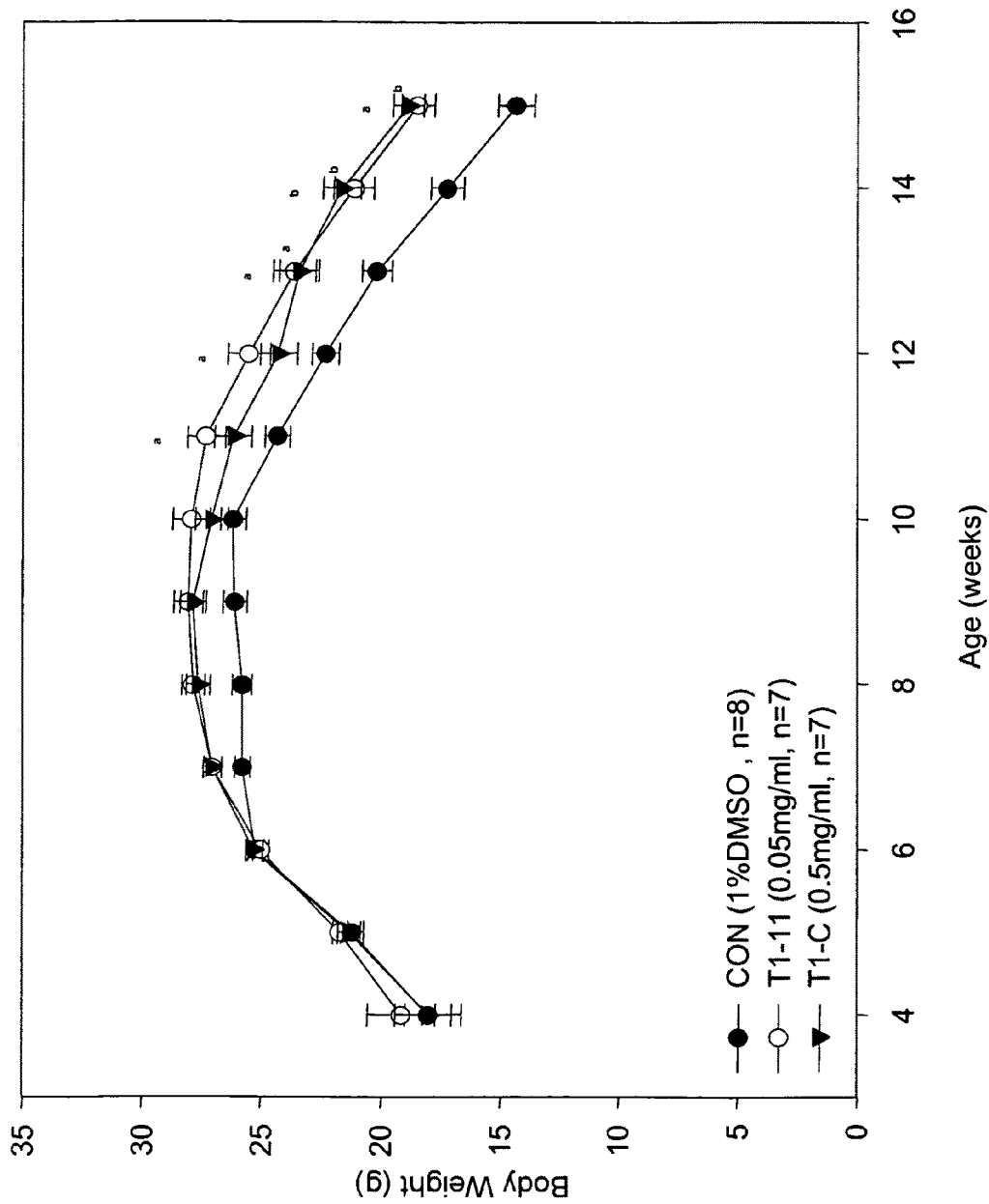
FIG. 8B is a graph showing body weight in R6/2 mice were given the control (CON, 1% DMSO, n=8), T1-C (0.5 mg/mL in 1% DMSO, n=7) or T1-11 (0.05 mg/mL in 1% DMSO, n=8)-containing drinking water from the age of 4 weeks.
Figure 8C:
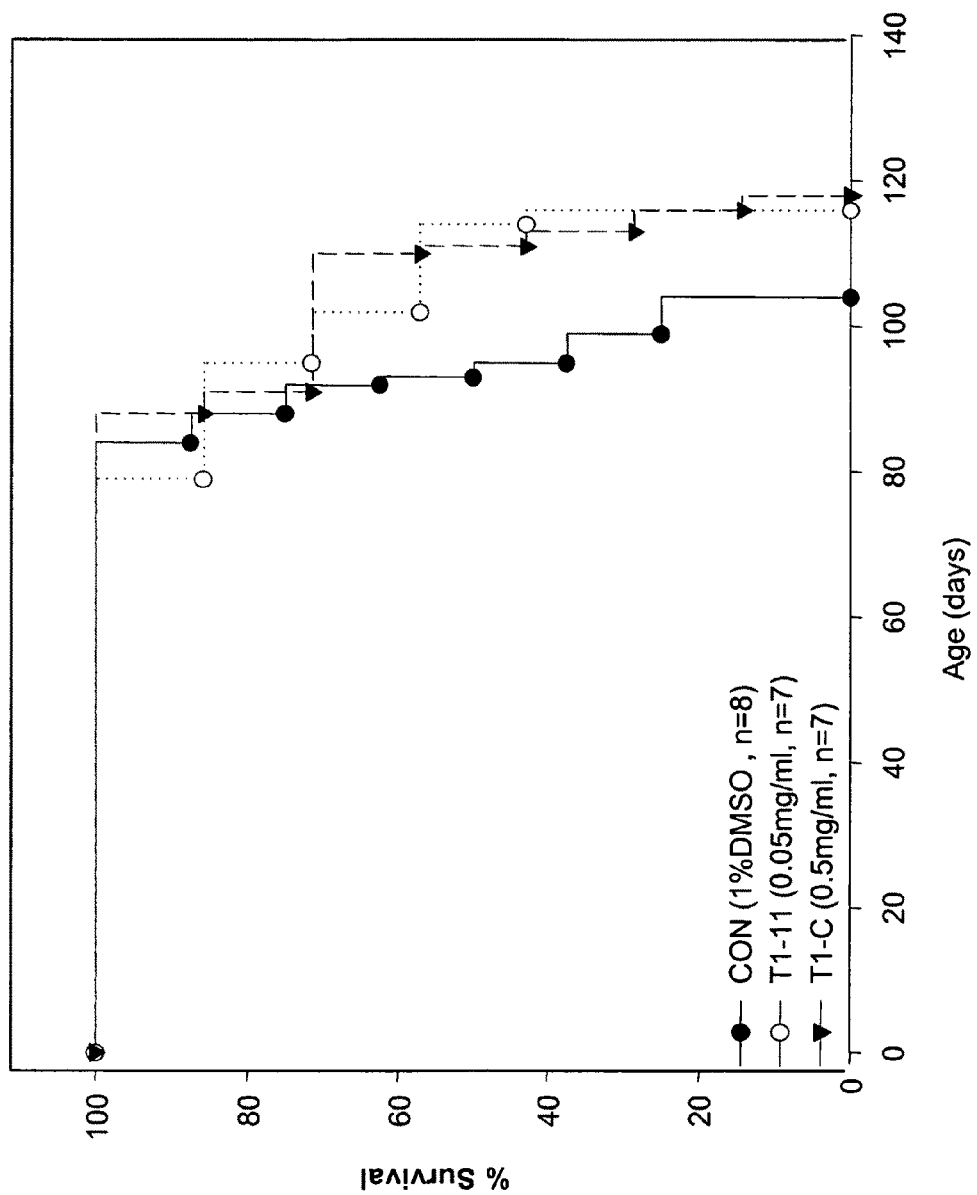
FIG. 8C is a graph showing survival percentage in R6/2 mice were given the control (CON, 1% DMSO, n=8), T1-C (0.5 mg/mL in 1% DMSO, n=7) or T1-11 (0.05 mg/mL in 1% DMSO, n=8)-containing drinking water from the age of 4 weeks.

Isolated Components of Active *Gastrodia elata* Extracts Maintain Motor Performance, Reduce Weight Loss, and Prolong Lifespan in R6/2 Mice Administration of either T1-C (0.5 mg/mL) or T1-11 (0.05 mg/mL) in the drinking water from the age of 4 weeks old markedly delayed the progressive deterioration of motor coordination of R6/2 mice assessed by rotarod performance (FIG. 8A). In addition, both compounds ameliorated the body weight loss and elongated the lifespan of R6/2 mice. The mean survival times of the control, T1-C and T1-11-treated mice were 94.9±2.5, 106.7±4.6 and 104.9±5.2 days (mean±SEM, n=7~8; FIG. 8C), respectively.

Example 8

Structure and Properties of Isolated Components of Active *Gastrodia elata* Extracts The structures of these two active components (T1-C and T1-11) were elucidated by analysis of spectroscopic data, especially 1D- and 2D-NMR spectral data. High-performance liquid chromatography was used to monitor the chemical profiles of different batches of the active fractions. The chromatogram of the active fraction showed the separation of the constituents with retention times of 40.91 min for T1-C and 22.03 min for T1-11.

T1-C was isolated as colorless needles having a molecular formula of $C_{14}H_{14}O_2S$ by HREIMS at m/z 247.0751 ($M^+ +H$) and $^{13}C$ NMR spectral data, with an eight-hydrogen deficiency (IHD). The IR spectrum showed the presence of hydroxyl group (3285 $cm^{-1}$) and aromatic (1604 and 1600 $cm^{-1}$) absorptions. An analysis of NMR and MS spectral data revealed the structure of T1-C to be a symmetrical compound. The $^1H$ NMR spectrum indicated a 1,4-disubstituted phenyl [δ 7.09 and 6.72 (4H each, d, J=8.5 Hz)] and two benzylic thiomethylene protons [δ 3.53 (4H, s)]. The $^{13}C$ NMR, DEPT and HMQC analyses revealed two oxygenated $sp^2$ aromatic carbons [6157.4 (s)], six aromatic carbons with two fully substituted $sp^2$ carbons, and two thiomethylene carbons. The HMBC spectrum of T1-C revealed cross peaks from H-7 to C-1, C-2(6); from H-2(6) to C-1, C-3(5), and C-4. From the above results, the structure of compound T1-C was established to be 4,4'-dihydroxybenzyl sulfide:

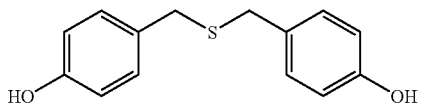

T1-C: mp 126~128° C.; IR (KBr) max: 3285, 1604, 1600, 1509, 1214, 1089, 841, 815 $cm^{-1}$; $^1H$ NMR ($CD_3OD$) δ 3.53 (4H, s, H-7), 6.72 and 7.09 (4H each, d, J=8.5 Hz, H-3(5) and H-2(6)); $^{13}C$ NMR ($CD_3OD$) δ 35.9 (t, C-7), 116.1 (d, C-3 (5)), 130.5 (s, C-1), 131.1 (d, C-2(6)), 157.4 (s, C4); EIMS m/z (%) 246 (M+, 35), 200 (15), 107 (100). HREIMS m/z 246.0717 (calcd for $C_{14}H_{14}O_2S$: 246.0715).

A compound with the same structure of T1-C has been documented earlier in a chemical analysis of *Gastrodia elata* extracts (Xiao, et al. (2002). In contrast, T1-11 appears not to have been identified before, and was isolated as a colorless amorphous powder with the molecular formula of $C_{17}H_{19}O_5N_5$ from HRFABMS at m/z 374.1361 ($M^+ +H$) and $^{13}C$ NMR spectral data. The IR spectrum suggested the presence of hydroxyls (3327, 1125, 1065, $cm^{-1}$), and an aromatic system (1630, 1610, 1585 $cm^{-1}$). The $^1H$ and $^{13}C$ NMR spectra showed a pattern similar to that of adenosine with the exception of signals due to a p-hydroxybenzylamino moiety [$δ_H$ 4.60 (2H, t, J=6.0 Hz), 6.65 and 7.12 (2H each, d, J=8.5 Hz, H-3"(5") and H-2"(6")); $δ_C$ 42.4 (t, H-7"), 114.9 (d, C-3" (5")), 128.6 (d, C-2"(6")), 130.8 (s, C-1")] instead of an amino group in T1-11. The linkage of the p-hydroxybenzylamino group was further determined from HMBC correlations between H-7" and C-1", C-2"(6"), and C-6. The structure of T1-11 (2-(6-(4-hydroxybenzylamino)-9H-purin-9-yl)-5-(hydroxymethyl)tetrahydrofuran-3,4-diol) is shown below:

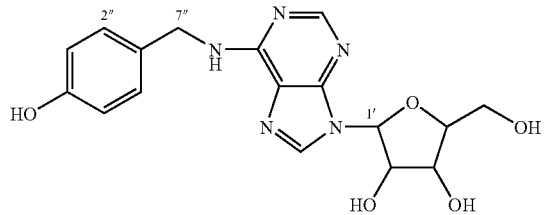

T1-11: mp 216~218° C.; IR (KBr) max: 3327, 3164, 2927, 1630, 1514, 1125, 1065, 815 $cm^{-1}$; $^1H$ NMR (DMSO-$d_6$) δ 3.54 and 3.64 (1H each, m, H-5'), 3.95 (1H, t, J=1.8 Hz, H-4'), 4.13 (1H, m, H-3'), 4.60 (3H, m, H-2', -7"), 5.87 (1H, d, J=5.5 Hz, H-1'), 6.65 and 7.12 (2H each, d, J=8.5 Hz, H-3"(5") and H-2"(6")), 8.19 and 8.33 (1H each, s, H-2 and H-8), 8.28, 9.19 (1H each, br s, OH and NH); $^{13}C$ NMR (DMSO-$d_6$) δ 42.4 (t, C-7"), 61.7 (t, C-5'), 70.7 (d, C-3'), 73.5 (d, C-2'), 85.9 (d, C4'), 88.0 (d, C-1'), 114.9 (d, C-3" (5")), 120.4 (s, C-5), 128.6 (d, C-2"(6")), 130.8 (s, C-1"), 139.8 (d, C-8), 148.4 (s, C4), 152.3 (d, C-2), 154.5 (s, C-6), 156.1 (s, C4"); FABMS m/z (%) 374 (M++1, 28), 242 (15), 154 (95), 136 (83), 56 (100); HRFABMS m/z 374.1361 (calcd for $C_{17}H_{19}O_5N_5$: 374.1388).

Example 8

Synthetic Schemes for Compounds

The compounds described herein can also be obtained by standard chemical synthetic methods starting from readily available starting materials. One exemplary synthetic scheme is shown below. In a coupling step, starting materials with precursor groups $X^1$ and $X^2$ are coupled to form the linker X:

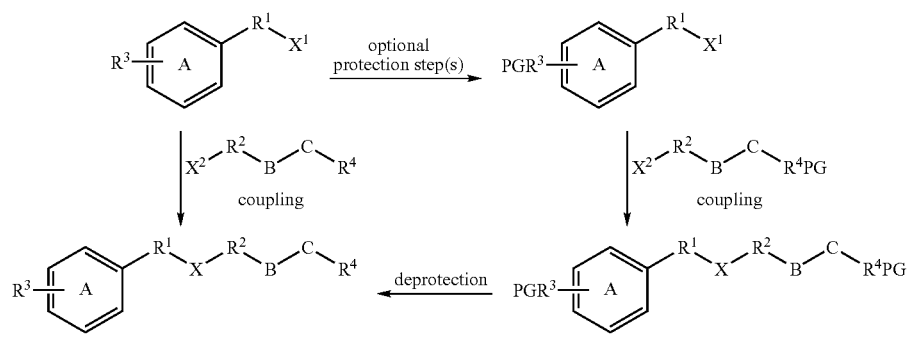

For example, compounds where X is —O— can be formed by selecting a pair of values for $X^1/X^2$ such as hydroxyl and halogen or metal hydroxide and halogen, and reacting under conditions suitable for ether formation (e.g., Larock, R. C. (1999, pages 890-895). Similarly, compounds where X is —S— can be formed by selecting values for $X^1/X^2$ such as thiol or thioolate and a leaving group such as halogen; such compounds can be further oxidized to convert —S— to —S(O)— or —$SO_2$—. Compounds where X is —C(O) $NR^a$—, —$NR^aC(O)$—, —$NR^aSO_2$—, or —$SO_2NR^a$— can be prepared from starting materials where one of $X^1$ and $X^2$ is an amine and the other is an amine-reactive carbonyl or sulfonyl derivative, for example, an acid halide, a sulfonyl halide, or the like, and reacting under conditions suitable for amide or sulfonamide formation (e.g., Larock, R. C. (1999, pages 1953-1954). Compounds where X is a disulfide can be prepared when $X^1/X^2$ are both —SH by reduction and purification. Compounds where X is —$NR^a$— can be prepared by selecting values for $X^1/X^2$ such as amine and halogen and reacting under conditions suitable for amine alkylation or arylation (Larock, R. C. (1999, pages 779-784).

Depending on the reaction conditions, the $R^3$ and $R^4$ groups can proceed through the reaction unmodified or can optionally be protected to form PG-$R^3$ and PG-$R^4$, where each PG is an appropriate protecting group. For example, when $R^3$ and $R^4$ are —OH, protecting groups can include alkyl ethers, alkoxyalkyl ethers, silyl ethers, or the like.

Standard reactions can be used to convert substituents such as $R^3$ and $R^4$ from readily available values, such as halogen, hydroxy, and the like, to other values. See, for example, Larock, 1999.

Example 9

Synthetic Route to T1

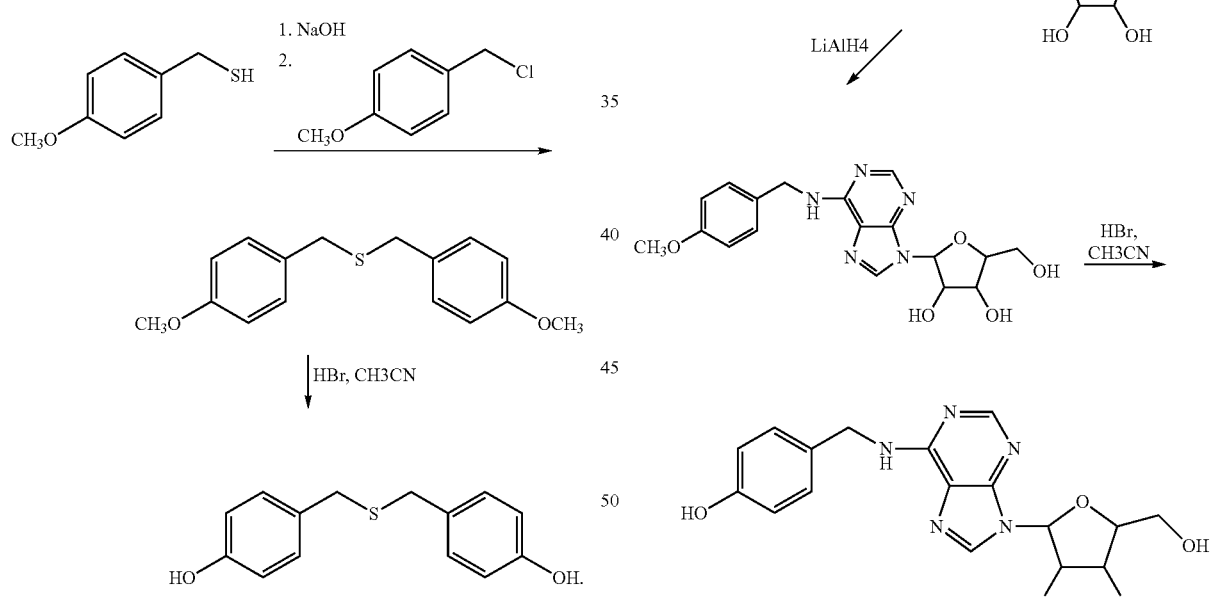

(4-methoxyphenyl)methanethiol is stirred in ethanol with sodium hydroxide to form sodium (4-methoxyphenyl)methanethiolate. An equivalent of 1-(chloromethyl)-4-methoxybenzene is added to the mixture, which is stirred overnight. The reaction mixture is then quenched by addition of dilute acid and the product bis(4-methoxybenzyl)sulfide. Subsequently, the bis(4-methoxybenzyl)sulfide is reacted with HBr in acetonitrile to cleave the methoxy protecting groups, followed by neutralization and purification of the bis(4-hydroxybenzyl)sulfide product.

Example 10

Synthetic Route to T1-11

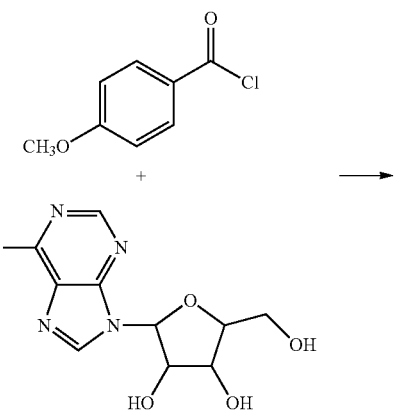

Adenine ribonucleoside (2-(6-amino-9H-purin-9-yl)-5-(hydroxymethyl)tetrahydrofuran-3,4-diol) and 4-methoxybenzoyl chloride are reacted together in methylene chloride overnight. Subsequently, the reaction is worked up and the benzoyl ketone moiety is reduced to methylene by reaction with a slight excess of lithium aluminum hydride in ethanol. The resulting compound is deprotected with HBr in acetonitrile to form the 2-(6-(4-hydroxybenzylamino)-9H-purin-9-yl)-5-(hydroxymethyl)tetrahydrofuran-3,4-diol product (T1-11).

Example 11

Effect of T1-11 on Inflammation

Methods and Materials:
Cell Culture:

Primary astrocytes were purified from neonatal (1-2-day old) brains of R6/2 HD mice (Mangiarini, L., et al., Exon 1 of the HD gene with an expanded CAG repeat is sufficient to cause a progressive neurological phenotype in transgenic mice. Cell 87, 493-506 (1996)) and their littermates as the WT control. In brief, the cortexes were carefully removed, digested with 0.05% trypsin-EDTA (Gibco, Grand Island, N.Y., USA) at 37° C. for 10 min, then mechanically dissociated by gentle pipetting and passed through a 70-µm-pore nylon mesh. Cell were plated onto poly-L-lysine-coated dishes and grown in Dulbecco's modified Eagle medium (DMEM; Gibco) supplemented with 10% v/v heat-inactivated fetal bovine serum (FBS), and 1% penicillin/streptomycin at 37° C. in a humidified 5% $CO_2$-containing atmosphere. Offspring were identified by a PCR-based genotyping technique of genomic DNA extracted from mice tails using the primers (5'-CCGCTCAGGTTCTGCTTTTA-3' (SEQ ID NO: 1) and 5'-GGCTGAGGAAG-CTGAGGAG-3'(SEQ ID NO: 2)) suggested by Jackson Laboratory. Mutant Htt expression was measured by a mouse monoclonal anti-human Htt antibody (EM48) (1:200 dilution, Chemicon International, Temecula, Calif., USA). The purity of the primary astrocyte cultures was determined by immunocytochemical staining using an antibody against an astrocyte-specific marker (GFAP, dilution 1:1000; Sigma, St. Louis, Mo., USA) or a microglia-specific marker (anti-CD11b, dilution 1:200, Serotec, Oxford, UK). At 30 DIV, 99% of the primary cultured cells were GFAP-positive. No detectable CD11b-positive cells (i.e., microglia) were found (data not shown). The microglia cell line (BV2, Mazzolla, R., et al. Enhanced resistance to *Cryptococcus neoformans* infection induced by chloroquine in a murine model of meningoencephalitis. *Antimicrob Agents Chemother* 41, 802-807 (1997)) was a generous gift from Dr. S F Tzeng (National Cheng Kung University, Tainan, Taiwan) and maintained in DMEM/F12 (Gibco, CA, USA) supplemented with 10% FBS (Hy-Clone) in an incubation chamber gassed with 5% CO2 and 95% air at 37° C.
Sodium Dodecylsulfate (SDS)-Polyacrylamide Gel Electrophoresis and Western Blotting:

Protein concentrations were determined using the Bio-Rad Protein Assay Dye Reagent Concentrate (Bio-Rad, Hercules, Calif., USA). Samples were loaded and separated on 8% SDS-polyacrylamide gels. Following electrophoresis, the gels were transferred to nitrocellulose membranes and blocked with 3% BSA in PBS and probed with the indicated antibody at 4° C. overnight. The membranes were then incubated with a peroxidase-conjugated secondary antibody for 1 h at room temperature and washed 3 times with TBST (0.2 M Tris-base, 1.37 M NaCl, and 0.1% Tween 20). The immunoreactive bands were stained using a light-emitting nonradioactive method (ECL, Fujifilm, Tokyo, Japan). For Western blot analyses, we used 1:1000 dilution for the anti-iNOS (BD Bioscience, CA, USA).
Measurement of Nitric Oxide (NO):

For the measurement of NO production, cells (5×105 cells/well) were treated with lipopolysaccharide (LPS, 0.5 µg/ml) in the presence of the desired drug for 72 hr. NO production was assessed as the amount of accumulated NO2-, a stable end product of NO formation, in the medium using s modified Griess reagent (Sigma, Mo., USA) following the manufacturer's protocol. Medium were mixed with equal volumes of 1× modified Griess reagent for 15 min. The absorbance at 540 nm was then monitored. NO production was normalized with the amount of protein in the same well, and is expressed as percentages of signals from WT astrocytes in the control (non-treated) condition.

Results and Discussion:

Inflammation contributes to the pathology of various trauma and neuronal degeneration diseases including Huntington's disease (Calabrese, V., Boyd-Kimball, D., Scapagnini, G. & Butterfield, D. A. Nitric oxide and cellular stress response in brain aging and neurodegenerative disorders: the role of vitagenes. *In Vivo* 18, 245-267 (2004); Deckel, A. W. Nitric oxide and nitric oxide synthase in Huntington's disease. *J Neurosci Res* 64, 99-107 (2001)). The neuroinflammatory machinery therefore is an important drug target for many degeneration diseases (Sastre, M., Klockgether, T. & Heneka, M. T. Contribution of inflammatory processes to Alzheimer's disease: molecular mechanisms. *Int J Dev Neurosci* 24, 167-176 (2006); Blanco, A. M. & Guerri, C. Ethanol intake enhances inflammatory mediators in brain: role of glial cells and TLR4/IL-1RI receptors. *Front Biosci* 12, 2616-2630 (2007); Marchetti, B., et al. Glucocorticoid receptor-nitric oxide crosstalk and vulnerability to experimental parkinsonism: pivotal role for glia-neuron interactions. *Brain Res Brain Res Rev* 48, 302-321 (2005); Barbeito, L. H., et al. A role for astrocytes in motor neuron loss in amyotrophic lateral sclerosis. *Brain Res Brain Res Rev* 47, 263-274 (2004); and Beattie, M. S. Inflammation and apoptosis: linked therapeutic targets in spinal cord injury. *Trends Mol Med* 10, 580-583 (2004)).

In the brain, the major cell types responsible for inflammatory responses are astrocytes and microglia. We thus examined the effect of T1-11 on inflammation using primary astrocytes purified from wildtype (WT) and R6/2-J2 mice (a mouse model of Huntington's disease), and a microglia cell line (BV2). The expression level of inducible nitric oxide synthase (iNOS) and the production of nitric oxide (NO) were used as inflammation markers as proposed elsewhere (Barbeito, L. H., et al. A role for astrocytes in motor neuron loss in amyotrophic lateral sclerosis. *Brain Res Brain Res Rev* 47, 263-274 (2004)).

In several pathological inflammation processes (e.g., septic shock, multiple organ failure, and chronic ethanol intoxication), NO produces toxic factors such as peroxynitrite and thus plays a major role (Blanco, A. M. & Guerri, C. Ethanol intake enhances inflammatory mediators in brain: role of glial cells and TLR4/IL-1RI receptors. *Front Biosci* 12, 2616-2630 (2007); Chandra, A., Enkhbaatar, P., Nakano, Y., Traber, L. D. & Traber, D. L. Sepsis: emerging role of nitric oxide and selectins. *Clinics* 61, 71-76 (2006).)

Figure 9:
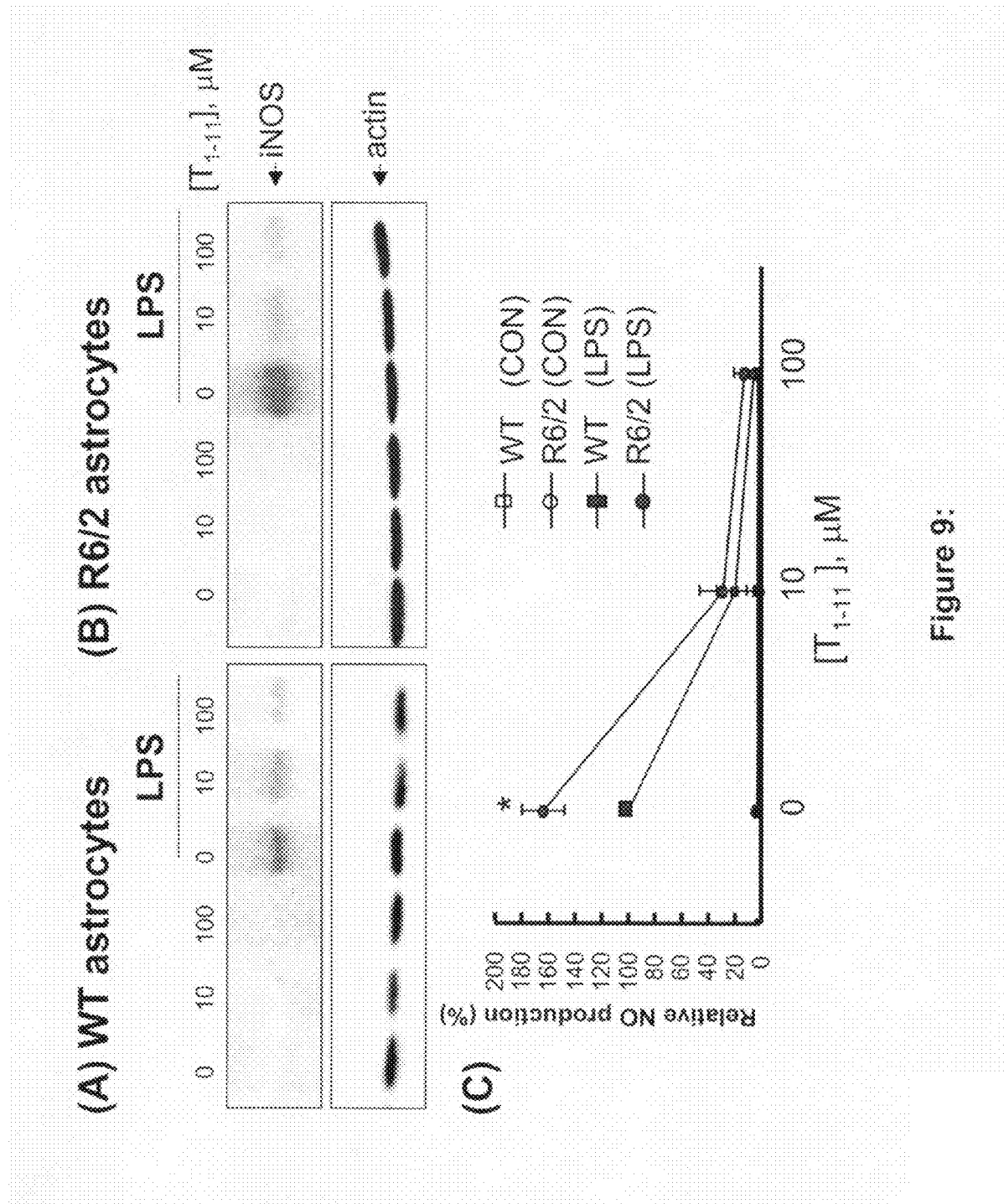
FIG. 9 shows that T1-11 effectively suppressed the LPS-induced inflammation.
Figure 10:
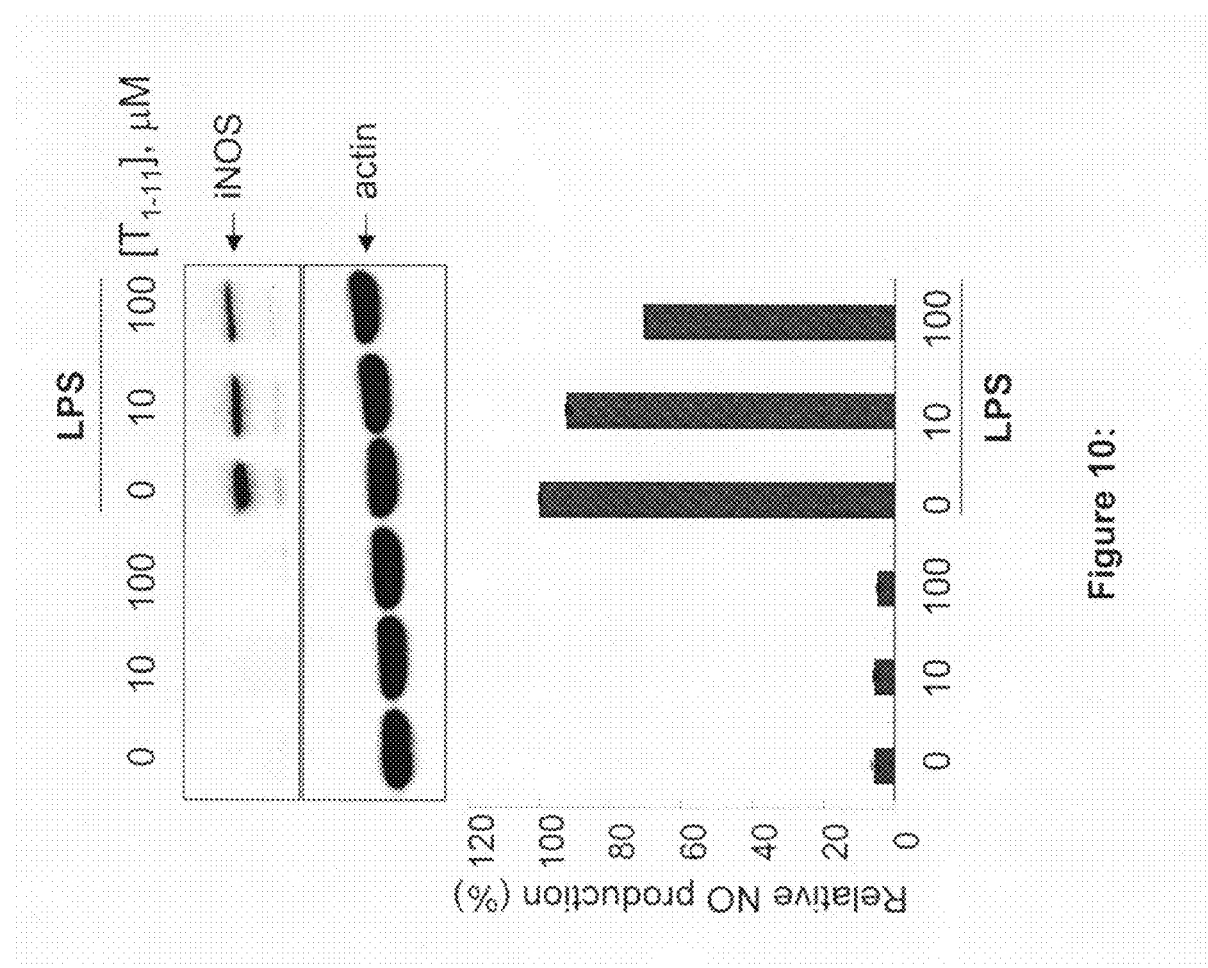
FIG. 10 shows that T1-11 reduces the LPS-evoked iNOS induction and NO production in BV2 cells.
Figure 11:
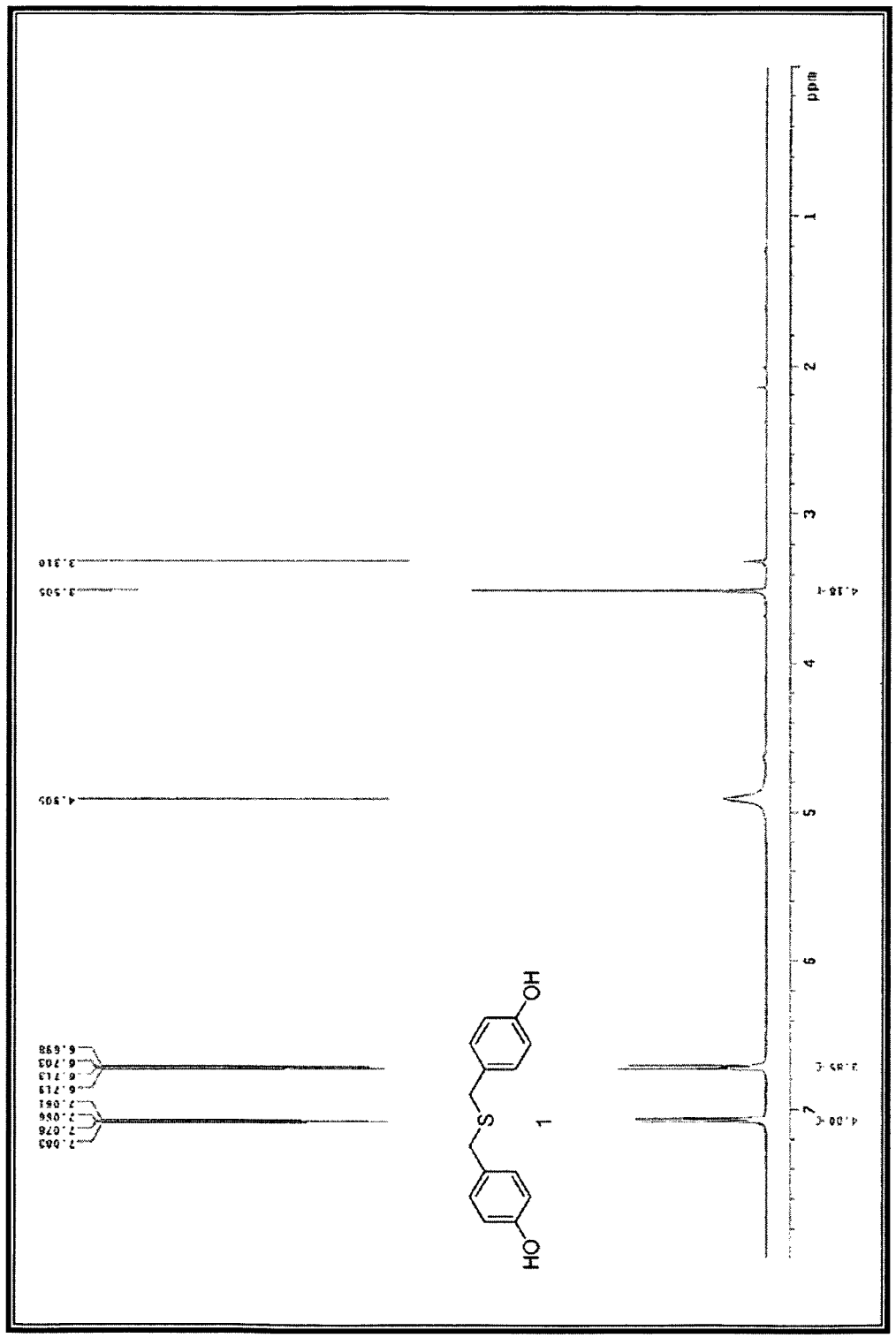
FIGS. 11-16 show $^1$H and $^{13}$C NMR spectra of compounds 1, 2 and 5.
Figure 12:
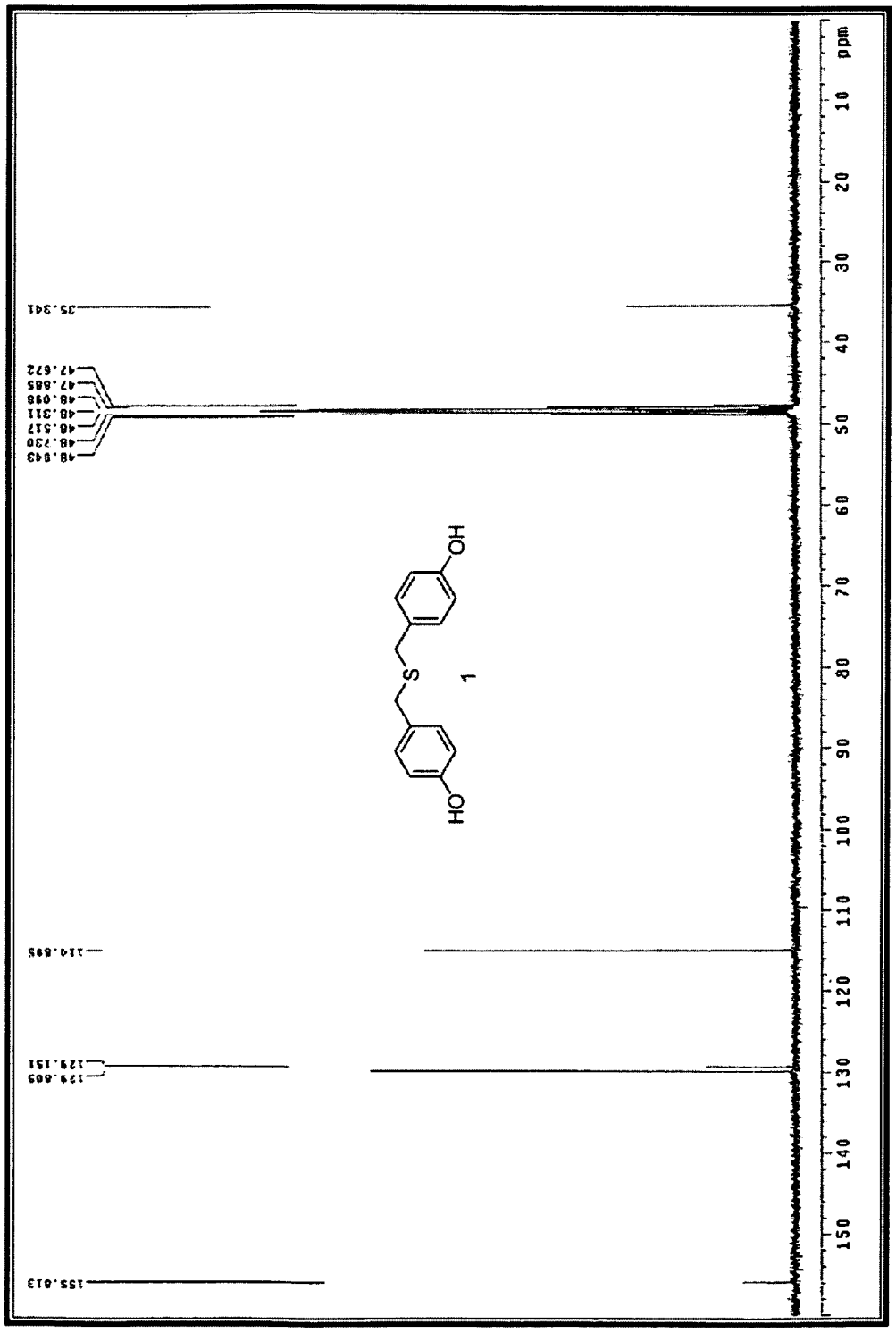
Figure 13:
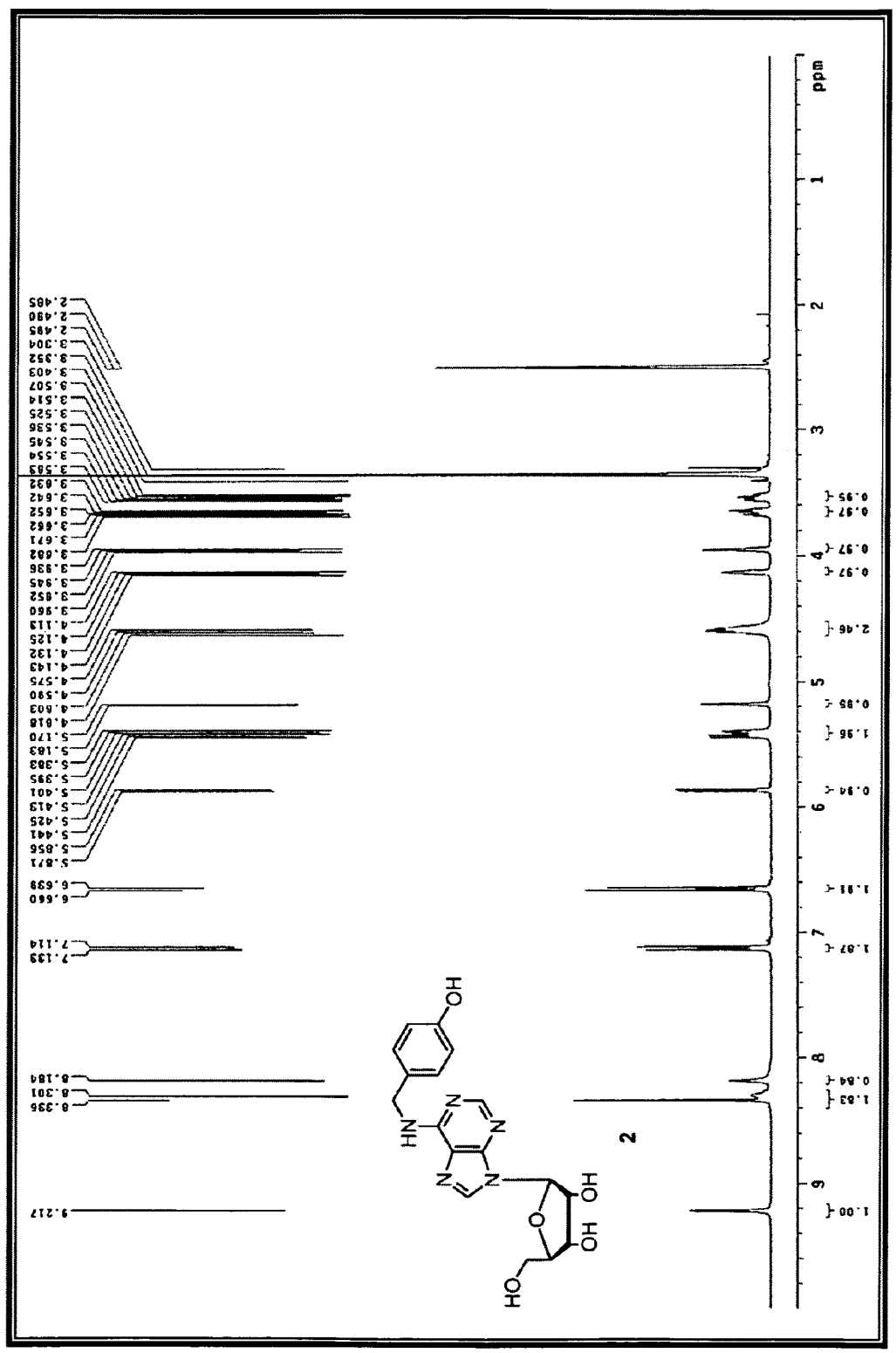
Figure 14:
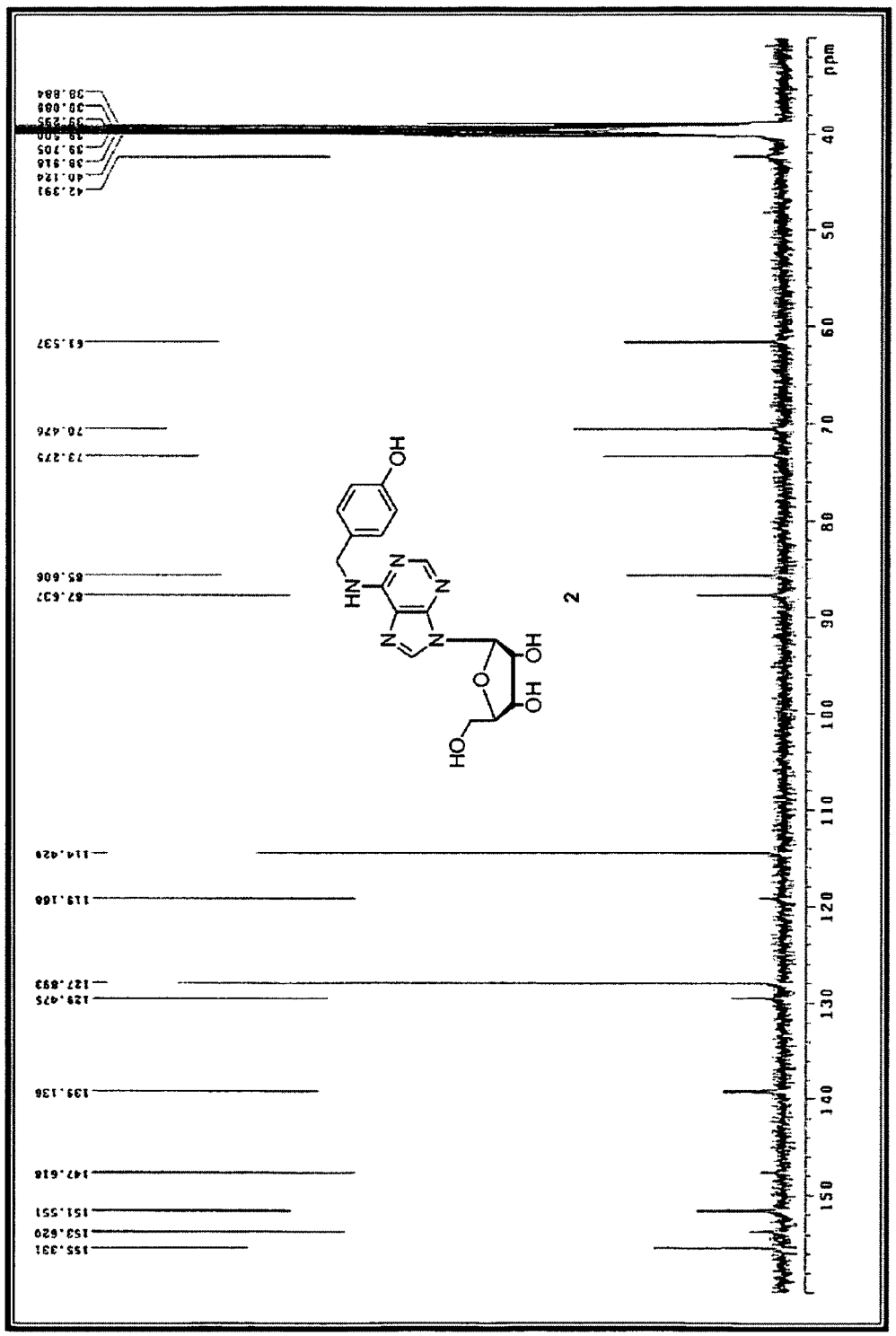
Figure 15:
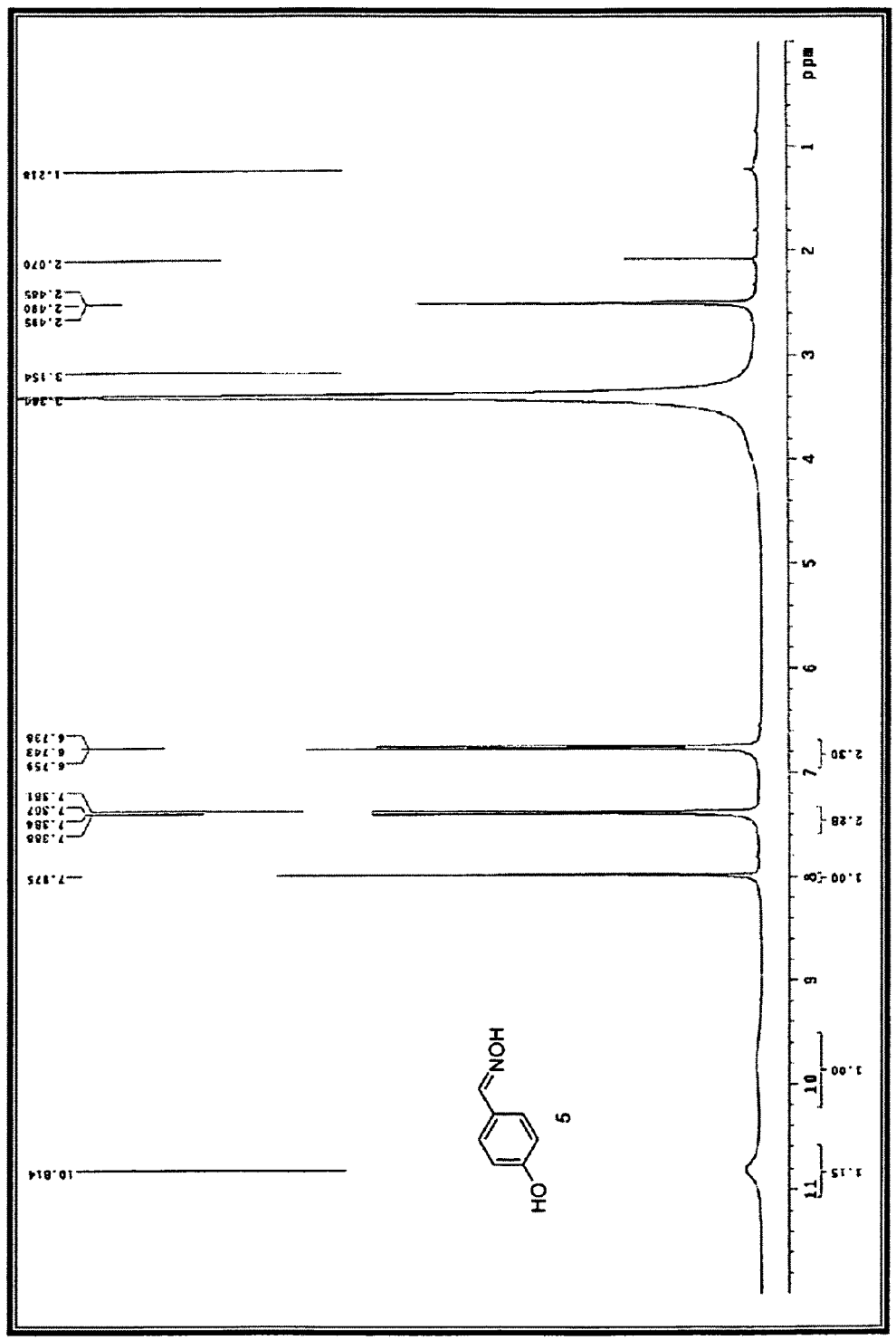
Figure 16:
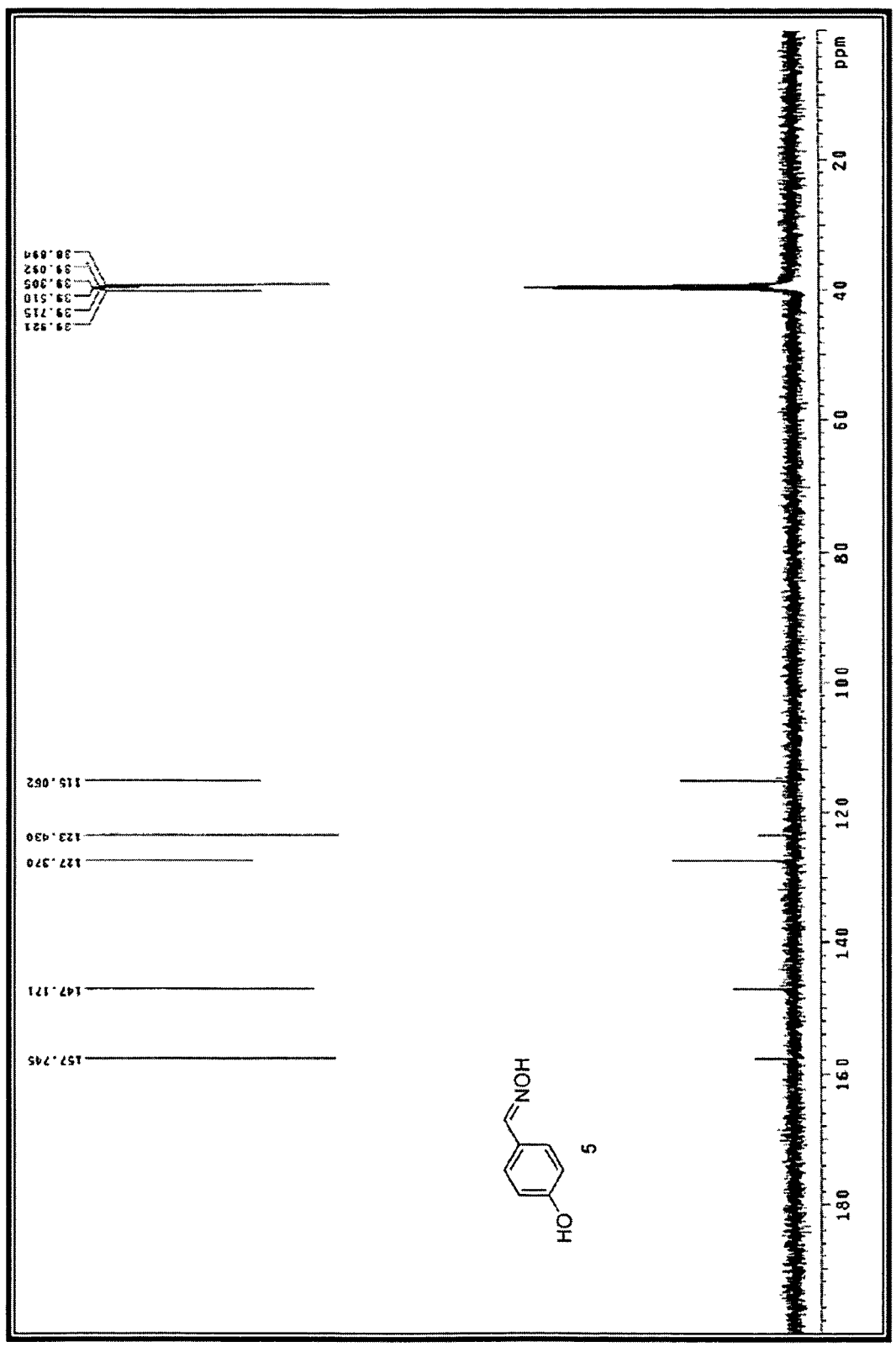

As shown in FIG. 9, low concentration of a bacterial toxin (lipopolysaccharide, LPS) markedly increased the expression of iNOS and NO production in astrocytes. Consistent with the hypothesis that chronic inflammation occurs in HD, primary astrocytes harvested from R6/2-J2 mice exhibited a higher expression of iNOS and NO production than those from wild-type mice. Most importantly, T1-11 effectively suppressed the LPS-induced inflammation (FIG. 9). Similarly, T1-11 also reduces the LPS-evoked iNOS induction and NO production in BV2 cells (FIG. 10). Since inflammatory responses associating with astrocyte recruitment and/or microglia activation have been implicated in many degeneration diseases (e.g., Alzheimer's disease, Parkinson's diseases, spinal cord injury, and amyotrophic lateral sclerosis), our finding herein suggest that T1-11 might produce beneficial effects on neuronal diseases/trauma involving inflammation, as well as other systematic crises (such as sepsis).

Example 12

Synthesis and Characterization of T1-11

Previously, two active compounds, T1-C (1) and T1-11 (2), have been purified from a Chinese herb, *Gastrodia elata*, and been characterized to exhibit neuroprotective effects (Huang, N. K., Lin, Y. L., Cheng, J. J. & Lai, W. L. *Gastrodia elata* prevents rat pheochromocytoma cells from serum-deprived apoptosis: the role of the MAPK family. *Life Sci* 75, 1649-1657 (2004); Huang, N. K., et al. Neuroprotective principles from *Gastrodia elata*. *J Nat Prod* 70, 571-574 (2007)).

The rhizomes of *G. elata* have been used as traditional Chinese medicine to improve memory, to ameliorate sleep disorder and to protect cardiac functions. Some researches have shown that *G. eleta* may prevent neuron from damage in several conditions (An, S. J., et al. Gastrodin decreases immunoreactivities of gamma-aminobutyric acid shunt enzymes in the hippocampus of seizure-sensitive gerbils. *J Neurosci Res* 71, 534-543 (2003); Kim, H. J., Moon, K. D., Oh, S. Y., Kim, S. P. & Lee, S. R. Ether fraction of methanol extracts of *Gastrodia elata*, a traditional medicinal herb, protects against kainic acid-induced neuronal damage in the mouse hippocampus. *Neurosci Lett* 314, 65-68 (2001); Kim, H. J., Lee, S. R. & Moon, K. D. Ether fraction of methanol extracts of *Gastrodia elata*, medicinal herb protects against neuronal cell damage after transient global ischemia in gerbils. *Phytother Res* 17, 909-912 (2003); Kim, H. J., Moon, K. D., Lee, D. S. & Lee, S. H. Ethyl ether fraction of *Gastrodia elata* Blume protects amyloid beta peptide-induced cell death. *J Ethnopharmacol* 84, 95-98 (2003); Hsieh, C. L., et al. Anticonvulsive and free radical scavenging activities of *Gastrodia elata* Bl. in kainic acid-treated rats. *Am J Chin Med* 29, 331-341 (2001); Hsieh, C. L., et al. Anticonvulsive and free radical scavenging activities of vanillyl alcohol in ferric chloride-induced epileptic seizures in Sprague-Dawley rats. *Life Sci* 67, 1185-1195 (2000)).

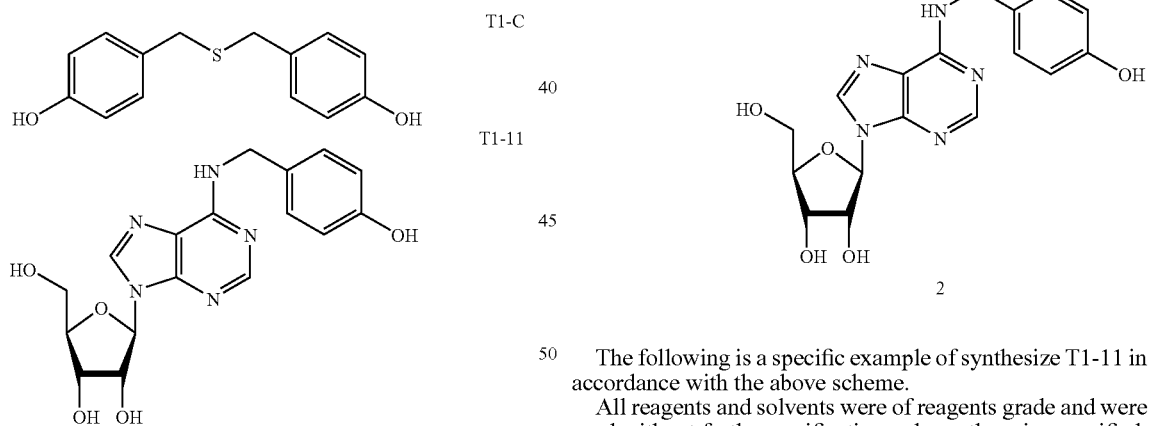

Because the content of T1-11 in the plant source is limited (~0.001% of dried plant material), we utilized organic synthesis as an essential approach to obtain sufficient T1-11 for further biological evaluation.

As shown in the following scheme, the adenosine analogue T1-11, compound 2, was synthesized in a high yield by the substitution reaction of 6-chloropurine ribonucleoside (7) with 4-hydroxybenzylamine hydrochloric salt (6) in the presence of a base of diisopropylethylamine (DIEA). Because the hydrochloric salt of amine 6 was not commercially available, it was prepared in two steps from 4-hydroxybenzaldehyde via the intermediacy of the corresponding oxime 5. Thus, the oxime was subjected to hydrogenation by the catalysis of 10% Pd/C to give the hydrochloric salt of amine 6. The $^1$H and $^{13}$C NMR spectra of compounds 1, 2, and 5 are illustrated in FIGS. 3-8. Those of the synthetic T1-11 were in agreement with the samples from natural sources (Calabrese, V., Boyd-Kimball, D., Scapagnini, G. & Butterfield, D. A. Nitric oxide and cellular stress response in brain aging and neurodegenerative disorders: the role of vitagenes. *In Vivo* 18, 245-267 (2004)).

Scheme of Synthesis of T1-11, $N^6$-(4-dihydroxybenzyl) aminopurine riboside.

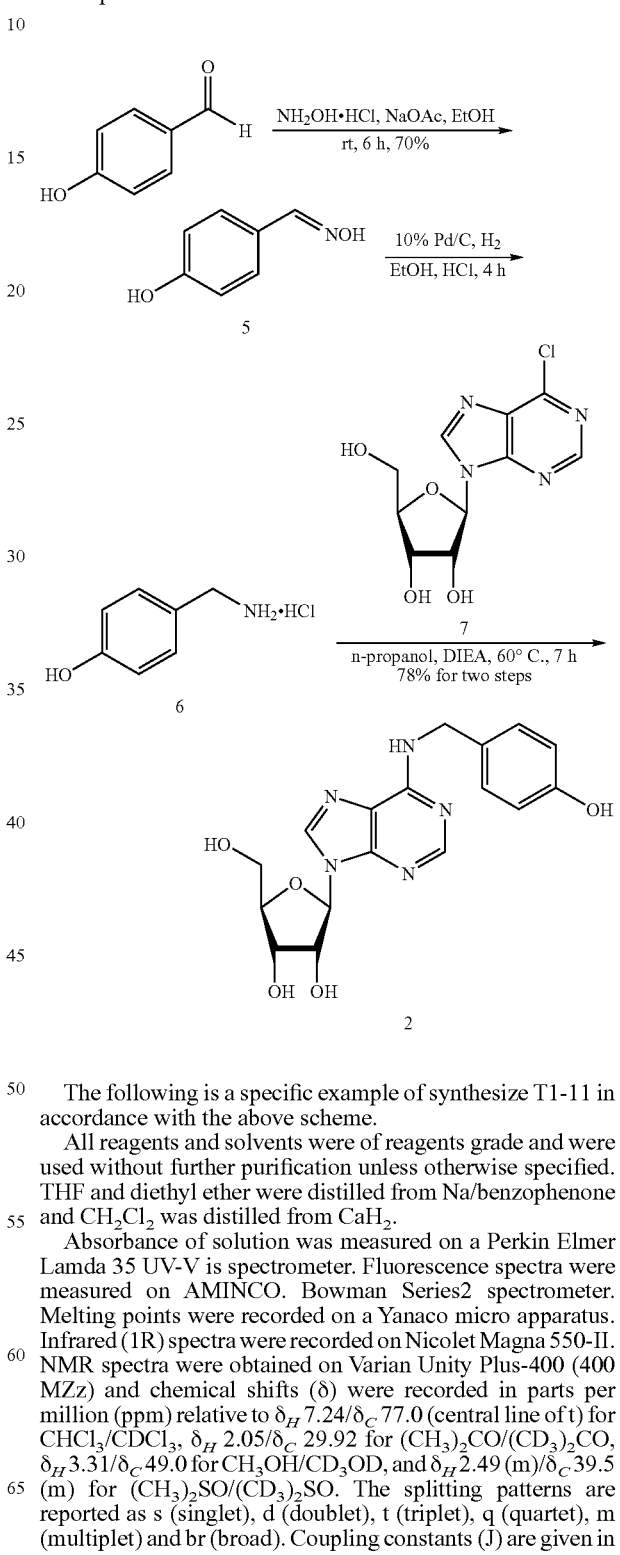

The following is a specific example of synthesize T1-11 in accordance with the above scheme.

All reagents and solvents were of reagents grade and were used without further purification unless otherwise specified. THF and diethyl ether were distilled from Na/benzophenone and $CH_2Cl_2$ was distilled from $CaH_2$.

Absorbance of solution was measured on a Perkin Elmer Lamda 35 UV-V is spectrometer. Fluorescence spectra were measured on AMINCO. Bowman Series2 spectrometer. Melting points were recorded on a Yanaco micro apparatus. Infrared (1R) spectra were recorded on Nicolet Magna 550-II. NMR spectra were obtained on Varian Unity Plus-400 (400 MZz) and chemical shifts (δ) were recorded in parts per million (ppm) relative to $\delta_H$ 7.24/$\delta_C$ 77.0 (central line of t) for $CHCl_3/CDCl_3$, $\delta_H$ 2.05/$\delta_C$ 29.92 for $(CH_3)_2CO/(CD_3)_2CO$, $\delta_H$ 3.31/$\delta_C$ 49.0 for $CH_3OH/CD_3OD$, and $\delta_H$ 2.49 (m)/$\delta_C$ 39.5 (m) for $(CH_3)_2SO/(CD_3)_2SO$. The splitting patterns are reported as s (singlet), d (doublet), t (triplet), q (quartet), m (multiplet) and br (broad). Coupling constants (J) are given in Hz. The ESI-MS experiments were conducted on a Bruker Daltonics BioTOF III high-resolution mass spectrometer. Analytical thin-layer chromatography (TLC) was performed on E. Merck silica gel 60 $F_{254}$ plates (0.25 mm). Compounds were visualized by UV, anisaldehyde or ninhydrin spray. Column chromatography was carried out on columns packed with 70-230 mesh silica gel.

All air or moisture sensitive experiments were performed under argon. All glasses were dried in oven for more than 2 hours and used after cooling to room temperature in desiccators.

$N^6$-(4-Hydroxybenzyl)adenosine (2) (Trivedi, B. K. B., C. J.; Bristol, J. A.; Hamilton, H. W.; Patt, W. C.; Kramer, W. J.; Johnson, S. A.; Bruns, R. F.; Cohen, D. M.; Ryan, M. J. N6-Substituted adenosine receptor agonists: potential antihypertensive agents. *J. Med. Chem.* 34, 1043-1049 (1991); Golisade, A. W., J.; Herforth, C.; Jomaab, H.; Linka, A. *Bioorg. Anti-malarial activity of $N^6$-substituted adenosine derivatives. Part I. Med. Chem.* 10, 769-777 (2002)).

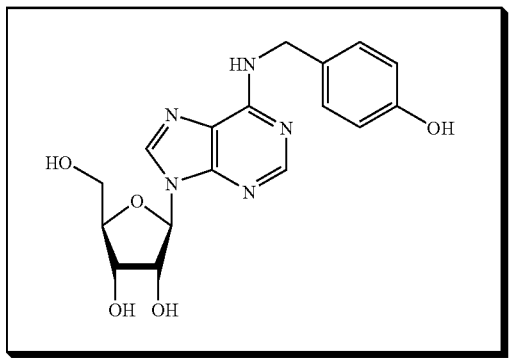

A 4-hydroxybenzylamine hydrochloric salt 6 (395 mg, 2.5 mmol), 6-chloro-purine ribonucleoside 7 (143 mg, 0.5 mmol), and diisopropylethylamine (2 mL, 12 mmol) in 1-propanol (25 mL) was heated to 70° C. for 6 h. The mixture was concentrated under reduced pressure, and triturated with water to give white precipitates, which were filtered to yielded the desired adenosine 2 (151 mg, 81%). $C_{17}H_{19}N_5O_5$; white powder, mp 208.7-209.2° C.; $[\alpha]^{20}_D = -64.5$ (DMSO, l=10 cm); TLC (MeOH/EtOAc (1:9)) $R_f$=0.3; $^1$H NMR (DMSO-$d_6$, 400 MHz) δ 9.22 (1H, s), 8.34 (1H, s), 8.30 (1H, br s), 8.18 (1H, s), 7.12 (2H, d, J=8.0 Hz), 6.65 (2H, d, J=8.0 Hz), 5.86 (1H, d, J=5.6 Hz), 5.41 (2H, m), 5.18 (1H, d, J=5.6 Hz), 4.60 (2H, m), 4.13 (1H, q, J=4.6, 7.4 Hz), 3.95 (1H, q, J=3.4, 6.2 Hz), 3.66 (1H, m), 3.53 (1H, m); $^{13}$C NMR (DMSO-$d_6$, 400 MHz) δ 155.3, 153.6, 151.6, 147.6, 139.1, 129.5, 127.9 (2×), 119.2, 114.4 (2×), 87.6, 85.6, 73.3, 70.5, 61.5, 42.4; ESI-MS calcd for $C_{17}H_{20}N_5O_5$: 374.1459, found: m/z 374.1412 ($M^+$+H).

Each document cited herein is incorporated by reference in its entirety.

A number of embodiments of the invention have been described. Nevertheless, it will be understood that various modifications may be made without departing from the spirit and scope of the invention. Other embodiments are within the scope of the following claims.

We claim:

1. A method of ameliorating or treating Huntington's disease in a mammalian subject in need thereof comprising administering the subject a pharmaceutical composition comprising an effective amount of purified or chemically synthesized $N^6$-(4-hydroxybenzyl)adenosine or a pharmaceutical salt or solvate thereof as a pharmaceutical active agent.

2. The method of claim 1 wherein $N^6$-(4-hydroxybenzyl)adenosine is a chemically synthesized compound.

3. The method of claim 1 wherein $N^6$-(4-hydroxybenzyl)adenosine is a purified compound.

4. A method of ameliorating or treating inflammation related to Huntington's disease in a mammalian subject in need thereof comprising administering the subject a pharmaceutical composition comprising an effective amount of purified or chemically synthesized $N^6$-(4-hydroxybenzyl)adenosine or a pharmaceutical salt or solvate thereof as a pharmaceutical active agent.

* * * * *